United States Patent
Sakano et al.

(10) Patent No.: US 11,261,551 B2
(45) Date of Patent: *Mar. 1, 2022

(54) SUTURING DEVICE PROVIDED WITH NEEDLE FOR HOLDING FIRST THREAD-LIKE MEMBER AND SHUTTLE FOR HOLDING SECOND THREAD-LIKE MEMBER

(71) Applicant: Brother Kogyo Kabushiki Kaisha, Nagoya (JP)

(72) Inventors: Yuji Sakano, Toyota (JP); Kohei Terada, Kiyosu (JP); Naokatsu Osawa, Nagoya (JP); Daisuke Ishii, Hiratsuka (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 221 days.

This patent is subject to a terminal disclaimer.

(21) Appl. No.: 16/280,344

(22) Filed: Feb. 20, 2019

(65) Prior Publication Data

US 2019/0233997 A1    Aug. 1, 2019

Related U.S. Application Data

(63) Continuation-in-part of application No. PCT/JP2017/029734, filed on Aug. 21, 2017.

(30) Foreign Application Priority Data

Aug. 22, 2016 (JP) .............................. JP2016-162286

(51) Int. Cl.
*A61B 17/06* (2006.01)
*D05B 57/10* (2006.01)
(Continued)

(52) U.S. Cl.
CPC ............ *D05B 57/10* (2013.01); *A61B 17/062* (2013.01); *D05B 23/00* (2013.01); *D05B 93/00* (2013.01); *D05B 61/00* (2013.01)

(58) Field of Classification Search
CPC ............ A61B 17/0469; A61B 17/0482; A61B 17/0485; A61B 17/0625
See application file for complete search history.

(56) References Cited

U.S. PATENT DOCUMENTS 4,417,532 A    11/1983   Yasukata
4,440,171 A *  4/1984    Nomoto ............. A61B 17/0491
                                                          112/169
(Continued)

FOREIGN PATENT DOCUMENTS

JP    S51-020393 U    2/1976
JP    S57-001332 A    1/1982
(Continued)

OTHER PUBLICATIONS

International Search Report and Written Opinion, International Application No. PCT/JP2017/029734, dated Oct. 31, 2017 (9 pages).

(Continued)

*Primary Examiner* — Alexander J Orkin
(74) *Attorney, Agent, or Firm* — Burr & Brown, PLLC

(57) ABSTRACT

A suturing device is provided, including a needle and a shuttle. The needle has an elongated shape extending in a predetermined direction and is configured to hold a first thread-like member. The needle is reciprocally movable forward and backward in the predetermined direction and is rotatable about an axis extending in the predetermined direction. Rotation of the needle about the axis permitting the first thread-like member to cross the needle to form a loop in the first thread-like member. The shuttle includes a holding portion. The holding portion is configured to hold a (Continued)

second thread-like member. The shuttle is configured to permit the holding portion to pass through the loop.

18 Claims, 29 Drawing Sheets

(51) Int. Cl.
  *A61B 17/062* (2006.01)
  *D05B 23/00* (2006.01)
  *D05B 93/00* (2006.01)
  *D05B 61/00* (2006.01)

(56) References Cited

U.S. PATENT DOCUMENTS

| | | | |
|---|---|---|---|
| 5,207,694 A | 5/1993 | Broomé | |
| 5,234,443 A * | 8/1993 | Phan | A61B 17/0469 606/144 |
| 5,336,230 A | 8/1994 | Leichtling et al. | |
| 5,417,700 A | 5/1995 | Egan | |
| 5,480,406 A | 1/1996 | Nolan et al. | |
| 5,496,334 A * | 3/1996 | Klundt | A61B 17/0491 606/139 |
| 5,984,932 A * | 11/1999 | Yoon | A61B 17/0469 606/147 |
| 6,004,332 A * | 12/1999 | Yoon | A61B 17/0469 606/139 |
| 7,144,401 B2 * | 12/2006 | Yamamoto | A61B 1/0008 606/144 |
| 7,416,556 B2 | 8/2008 | Jackson | |
| 11,020,106 B2 * | 6/2021 | Sakano | A61B 17/0469 |
| 2003/0139752 A1 * | 7/2003 | Pasricha | A61B 17/0469 606/139 |
| 2004/0092963 A1 * | 5/2004 | Moll | A61B 17/0491 606/144 |
| 2010/0228271 A1 * | 9/2010 | Marshall | A61B 17/0469 606/144 |
| 2011/0041745 A1 | 2/2011 | Mingazhev | |
| 2012/0143223 A1 * | 6/2012 | Woodard, Jr | A61B 17/29 606/147 |
| 2019/0231346 A1 * | 8/2019 | Sakano | D05B 23/00 |
| 2019/0233996 A1 * | 8/2019 | Sakano | D05B 23/00 |

FOREIGN PATENT DOCUMENTS

| | | |
|---|---|---|
| JP | S61-240994 A | 10/1986 |
| JP | 2013-240574 A | 12/2013 |

OTHER PUBLICATIONS

English translation of International Preliminary Report on Patentability (Chapter I) (Application No. PCT/JP2017/029734) dated Feb. 26, 2019, 6 pages.

* cited by examiner

FIG. 33

| No. | COMPONENT | STATUS | (a) | (b) | (c) | (d) | (e) | (f) | (g) | (h) | (i) | (j) |
|---|---|---|---|---|---|---|---|---|---|---|---|---|
| ① | NEEDLE THREAD | SUPPLY | | | | | | | | | | |
| | | HOLD | | | | | | | | | | |
| | | PULL | | | | | | | | | | |
| ② | NEEDLE | ADVANCED END | | | | | | | | | | |
| | | LOOP | | | | | | | | | | |
| | | DEPRESSION | | | | | | | | | | |
| | | RETRACTED END | | | | | | | | | | |
| | | CWR | | | | | | | | | | |
| | | REST | | | | | | | | | | |
| | | CCW | | | | | | | | | | |
| ③ | SHUTTLE | ADVANCED END | | | | | | | | | | |
| | | RETRACTED END | | | | | | | | | | |
| | | RIGHT STOP | | | | | | | | | | |
| | | LEFT STOP | | | | | | | | | | |
| ④ | PUSHER | RIGHTMOST END | | | | | | | | | | |
| | | RIGHT STOP | | | | | | | | | | |
| | | LEFT STOP | | | | | | | | | | |
| | | LEFTMOST END | | | | | | | | | | |
| ⑤ | HOOK MEMBER | ADVANCED END | | | | | | | | | | |
| | | ADVANCED | | | | | | | | | | |
| | | RETRACTED | | | | | | | | | | |
| | | RETRACTED END | | | | | | | | | | |
| | | CWR | | | | | | | | | | |
| | | REST | | | | | | | | | | |
| | | CCW | | | | | | | | | | |
| ⑥ | BALLOON | EXPAND | | | | | | | | | | |
| | | SHRINK | | | | | | | | | | |

FIG. 46

OPERATION PATTERN A

| No. | COMPONENT | STATUS | (k) | (l) | (m) | (n) | (o) | (p) | (q) | (r) | (s) | (t) |
|---|---|---|---|---|---|---|---|---|---|---|---|---|
| ① | NEEDLE THREAD | SUPPLY | | | | | | | | | | |
| | | HOLD | | | | | | | | | | |
| | | PULL | | | | | | | | | | |
| ② | NEEDLE | ADVANCED END | | | | | | | | | | |
| | | LOOP | | | | | | | | | | |
| | | DEPRESSION | | | | | | | | | | |
| | | RETRACTED END | | | | | | | | | | |
| | | CWR | | | | | | | | | | |
| | | REST | | | | | | | | | | |
| | | CCW | | | | | | | | | | |
| ③ | SHUTTLE | ADVANCED END | | | | | | | | | | |
| | | RETRACTED END | | | | | | | | | | |
| | | RIGHT STOP | | | | | | | | | | |
| | | LEFT STOP | | | | | | | | | | |
| ④ | PUSHER | RIGHTMOST END | | | | | | | | | | |
| | | RIGHT STOP | | | | | | | | | | |
| | | LEFT STOP | | | | | | | | | | |
| | | LEFTMOST END | | | | | | | | | | |
| ⑤ | HOOK MEMBER | ADVANCED END | | | | | | | | | | |
| | | ADVANCED | | | | | | | | | | |
| | | RETRACTED | | | | | | | | | | |
| | | RETRACTED END | | | | | | | | | | |
| | | CWR | | | | | | | | | | |
| | | REST | | | | | | | | | | |
| | | CCW | | | | | | | | | | |
| ⑥ | BALLOON | EXPAND | | | | | | | | | | |
| | | SHRINK | | | | | | | | | | |

FIG. 47

OPERATION PATTERN B

| No. | COMPONENT | STATUS | (k) | (l) | (m) | (n) | (o) | (p) | (q) | (r) | (s) | (t) |
|---|---|---|---|---|---|---|---|---|---|---|---|---|
| ① | NEEDLE THREAD | SUPPLY | | | | | | | | | | |
| | | HOLD | | | | | | | | | | |
| | | PULL | | | | | | | | | | |
| ② | NEEDLE | ADVANCED END | | | | | | | | | | |
| | | LOOP | | | | | | | | | | |
| | | DEPRESSION | | | | | | | | | | |
| | | RETRACTED END | | | | | | | | | | |
| | | CWR | | | | | | | | | | |
| | | REST | | | | | | | | | | |
| | | CCW | | | | | | | | | | |
| ③ | SHUTTLE | ADVANCED END | | | | | | | | | | |
| | | RETRACTED END | | | | | | | | | | |
| | | RIGHT STOP | | | | | | | | | | |
| | | LEFT STOP | | | | | | | | | | |
| ④ | PUSHER | RIGHTMOST END | | | | | | | | | | |
| | | RIGHT STOP | | | | | | | | | | |
| | | LEFT STOP | | | | | | | | | | |
| | | LEFTMOST END | | | | | | | | | | |
| ⑤ | HOOK MEMBER | ADVANCED END | | | | | | | | | | |
| | | ADVANCED | | | | | | | | | | |
| | | RETRACTED | | | | | | | | | | |
| | | RETRACTED END | | | | | | | | | | |
| | | CWR | | | | | | | | | | |
| | | REST | | | | | | | | | | |
| | | CCW | | | | | | | | | | |
| ⑥ | BALLOON | EXPAND | | | | | | | | | | |
| | | SHRINK | | | | | | | | | | |

FIG. 48

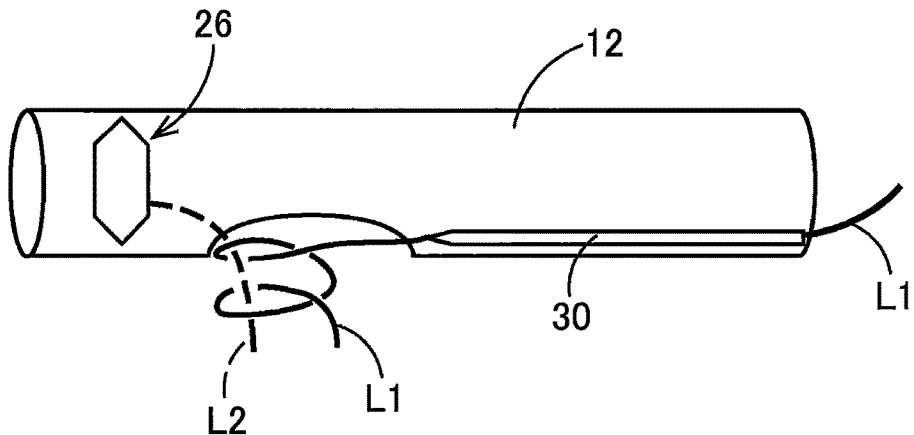

FIG. 49

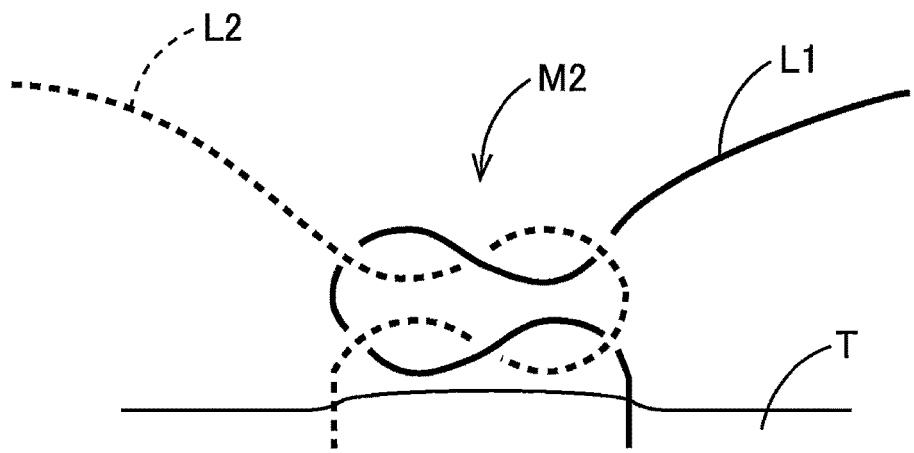

FIG. 50

| FIRST STAGE | | SECOND STAGE | | TYPE OF KNOT |
|---|---|---|---|---|
| OPERATION PATTERN A | NEEDLE CWR SHUTTLE CWR | OPERATION PATTERN A | NEEDLE CWR SHUTTLE CWR | GRANNY KNOT |
| OPERATION PATTERN B | NEEDLE CCW SHUTTLE CCW | OPERATION PATTERN B | NEEDLE CCW SHUTTLE CCW | GRANNY KNOT |
| OPERATION PATTERN A | NEEDLE CWR SHUTTLE CWR | OPERATION PATTERN B | NEEDLE CCW SHUTTLE CCW | SQUARE KNOT |
| OPERATION PATTERN B | NEEDLE CCW SHUTTLE CCW | OPERATION PATTERN A | NEEDLE CWR SHUTTLE CWR | SQUARE KNOT |

SUTURING DEVICE PROVIDED WITH NEEDLE FOR HOLDING FIRST THREAD-LIKE MEMBER AND SHUTTLE FOR HOLDING SECOND THREAD-LIKE MEMBER

CROSS REFERENCE TO RELATED APPLICATION

This application is a bypass continuation-in-part application of International Application No. PCT/JP2017/029734 filed Aug. 21, 2017 in the Japan Patent Office acting as Receiving Office, claiming priority from Japanese Patent Application No. 2016-162286 filed Aug. 22, 2016. The entire contents of each of these applications are incorporated herein by reference.

FIELD OF THE INVENTION

The present disclosure relates to a suturing device that secures thread-like members together with each stitch and forms stitches or knots in the thread-like members.

BACKGROUND OF THE INVENTION

Technologies have been proposed for forming a loop and a knot in thread-like members that have been passed through a suturing target and for immobilizing the suturing target, including a technology that uses a suture anchor configured of metal or synthetic resin to clamp thread-like members together (see U.S. Pat. No. 7,416,556), and a technology for interlocking uneven formations pre-formed in the thread-like member itself (see U.S. Pat. No. 5,207,694). A technology has also been proposed for welding thread-like members together using heat or ultrasound (see U.S. Pat. No. 5,417,700). However, thread-like members that are fixed by clamping together, interlocking, or welding the thread-like members have less binding strength and tightening ability than thread-like members that are tied together with a knot.

Accordingly, various methods of forming knots to secure thread-like members by tying the thread-like members themselves are well known, and various needle grasping devices, auxiliary tools, and the like for forming knots have been proposed.

One technology describes forming knots through an operation similar to a manual operation in which two grasping devices are simply manipulated to control their positional relationship (see U.S. Pat. No. 5,336,230). This technology essentially requires that both grasping devices be operated. Another device is an auxiliary suturing tool that forms knots by performing a prescribed procedure (see U.S. Pat. No. 5,480,406). This technology requires that another grasper be used for transferring the thread-like member, since a knot cannot be formed with the auxiliary suturing tool alone.

SUMMARY OF THE INVENTION

While various devices for tying thread-like members have been proposed, none of these devices is more than an auxiliary tool for aiding the operator in tying the thread-like members and none successfully realizes a device for forming knots easily and reliably through mechanical operations.

With all of the above conventional devices, a human operator must determine which side of what thread-like member to pass the grasper, when and where to grasp the thread-like member, how many times and in what direction to wrap the thread-like member, and the like and must perform such operations based solely on information the operator takes in visually and the like. Accordingly, the operator must have had sufficient training in advance and must have proficient technique in practice in order to form knots using these tools. In other words, all of these tools require skill and cannot be defined as devices that can form knots reliably through simple mechanical operations.

In view of the foregoing, it is an object of the present disclosure to provide a suturing device capable of easily and reliably forming stitches or knots through mechanical operations requiring only simple manipulations.

In order to attain the above and other objects, the present disclosure provides a suturing device that includes: a needle; and a shuttle. The needle has an elongated shape extending in a predetermined direction and configured to hold a first thread-like member. The needle is reciprocally movable forward and backward in the predetermined direction and is rotatable about an axis extending in the predetermined direction. Rotation of the needle about the axis permits the first thread-like member to cross the needle to form a loop in the first thread-like member. The shuttle includes a holding portion. The holding portion is configured to hold a second thread-like member. The shuttle is configured to permit the holding portion to pass through the loop.

BRIEF DESCRIPTION OF THE DRAWINGS

The particular features and advantages of the disclosure as well as other objects will become apparent from the following description taken in connection with the accompanying drawings, in which:

FIG. 33 is a timing diagram for describing timed-relational movements of respective components those involved in the single stitch forming operation illustrated in FIGS. 16 through 24 and FIGS. 25 through 32 in the suturing device according to the embodiment;

FIG. 46 is a timing diagram for describing timed-relational movements of respective components those involved in the half hitch forming operation illustrated in FIGS. 38 through 43 in the suturing device according to the embodiment, and particularly illustrating an operation pattern A in which the needle exhibits a right-hand rotation for winding the first thread-like member and the shuttle passed through the loop in the first thread-like member while moving in a right-hand circumferential direction;

FIG. 47 is a timing diagram for describing timed-relational movements of respective components those involved in the half hitch forming operation illustrated in FIGS. 38 through 43 in the suturing device according to the embodiment, and particularly illustrating an operation pattern B in which the needle exhibits a left-hand rotation for winding the first thread-like member and the shuttle passed through the loop in the first thread-like member while moving in a left-hand circumferential direction;

FIG. 48 is a schematic view illustrating a primitive form of a knot obtained by performing a half hitch forming operation at a first stage operation and a half hitch forming operation at a second stage operation different from the first stage operation in accordance with the half hitch forming operation attendant to FIGS. 38 through 43;

FIG. 49 illustrates a square knot produced by reshaping the primitive form of the knot illustrated in FIG. 48;

FIG. 50 is a table illustrating a relationship between the first stage operation patterns and the second stage operation patterns and types of produced knots;

DETAILED DESCRIPTION OF THE INVENTION

Figure 1:
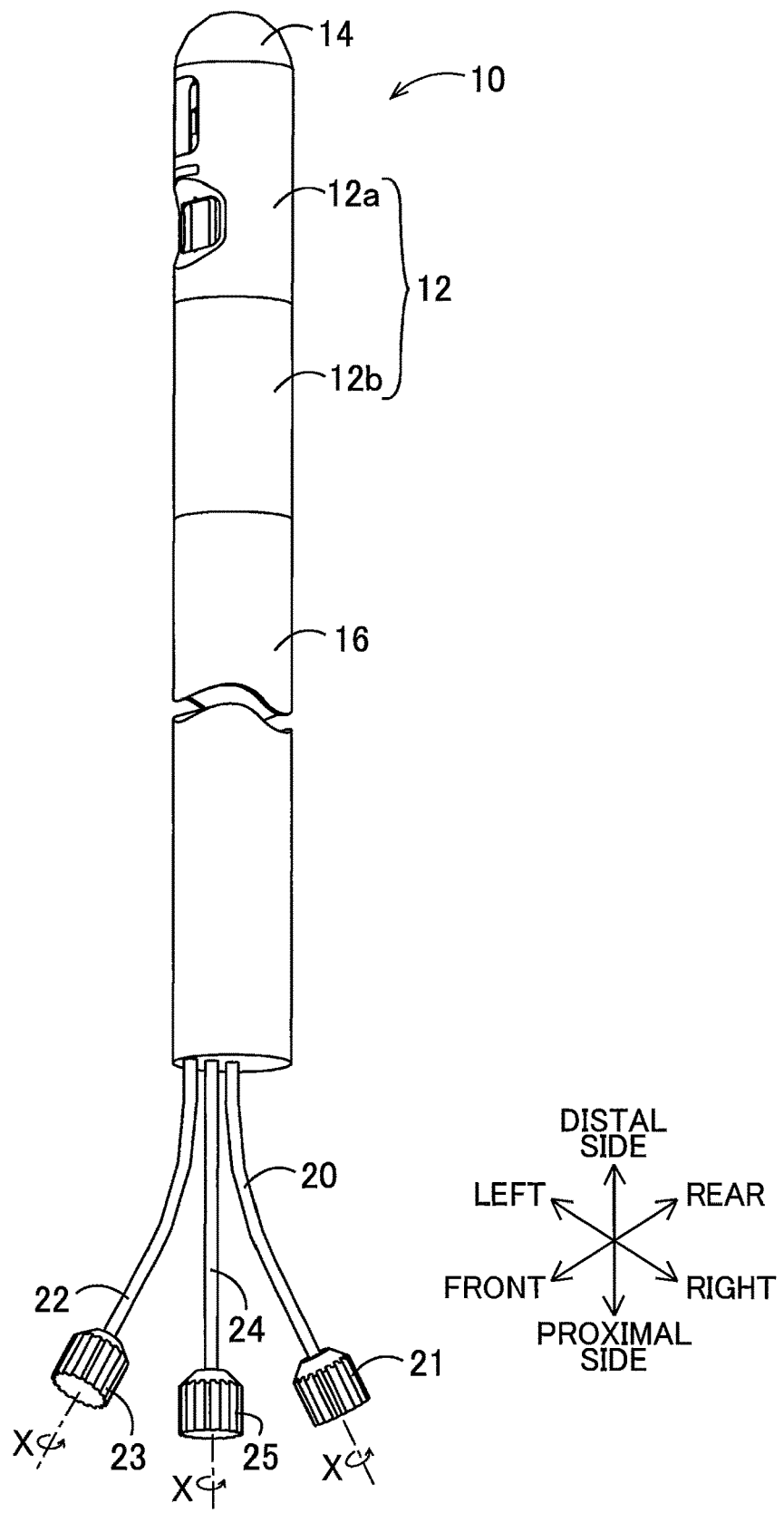
FIG. 1 is a perspective view illustrating an entire exterior of a suturing device according to one embodiment of the present disclosure.
Figure 2:
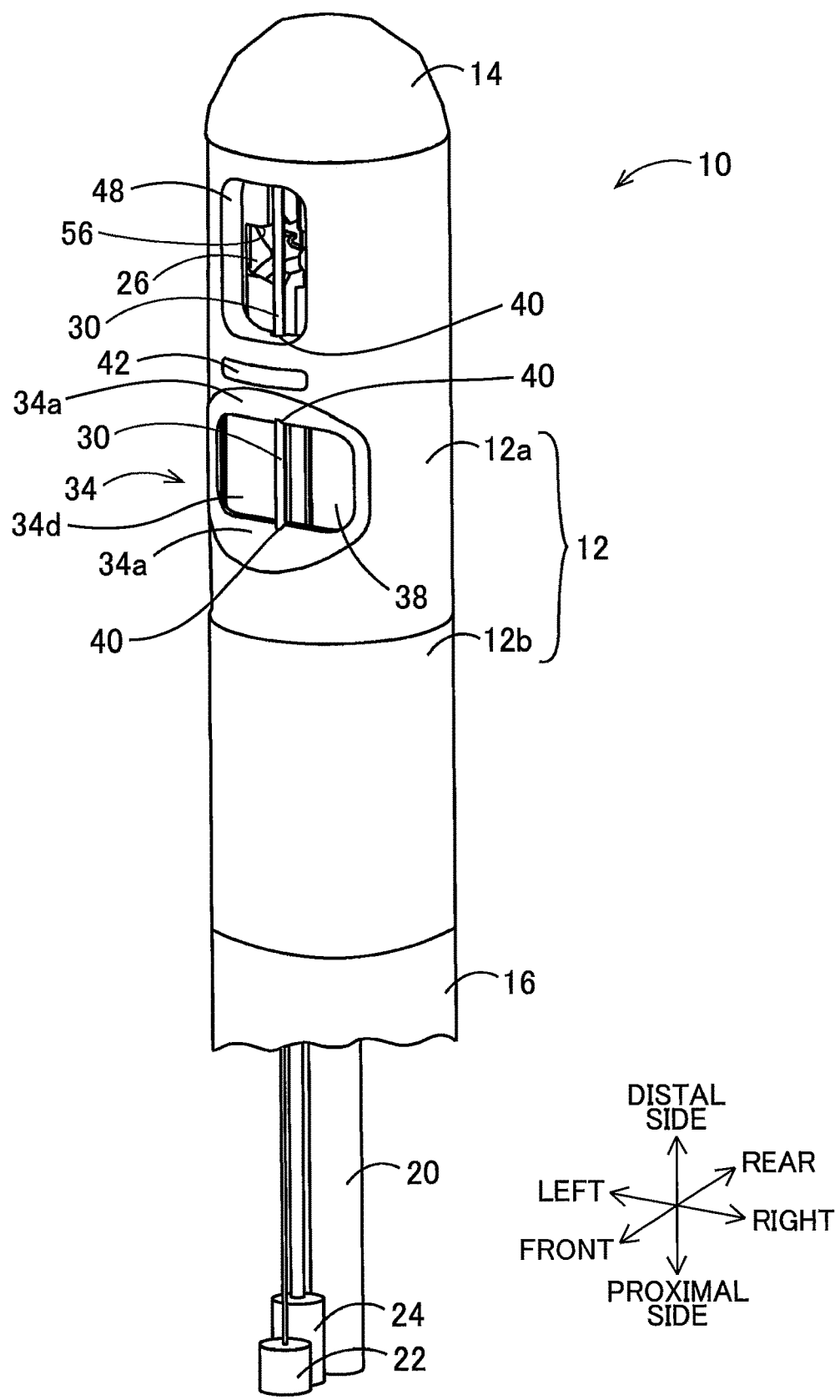
FIG. 2 is an enlarged perspective view illustrating a distal end portion of the suturing device according to the embodiment of the present disclosure.
Figure 3:
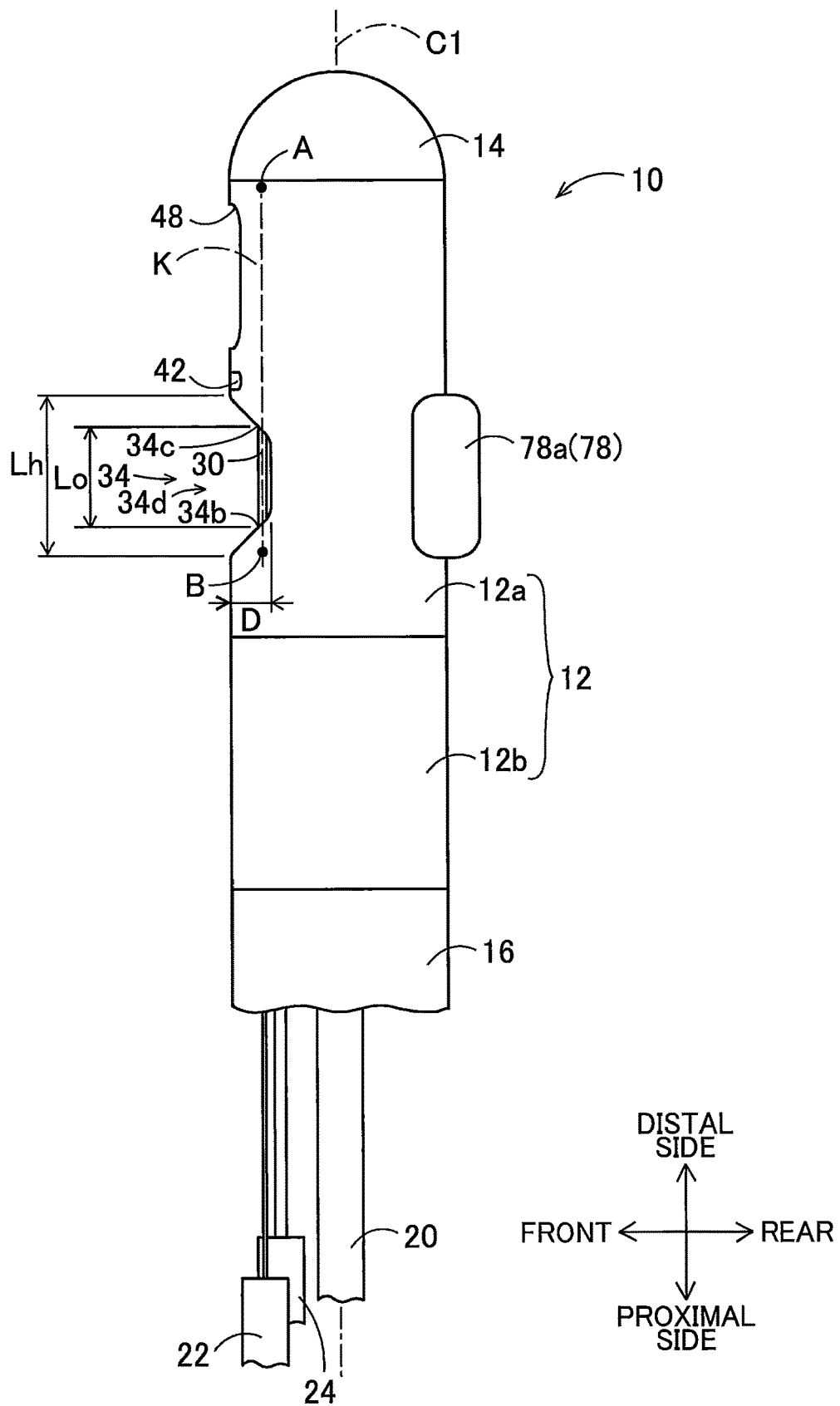
FIG. 3 is a side view of the distal end portion of the suturing device illustrated in FIGS. 1 and 2.
Figure 4:
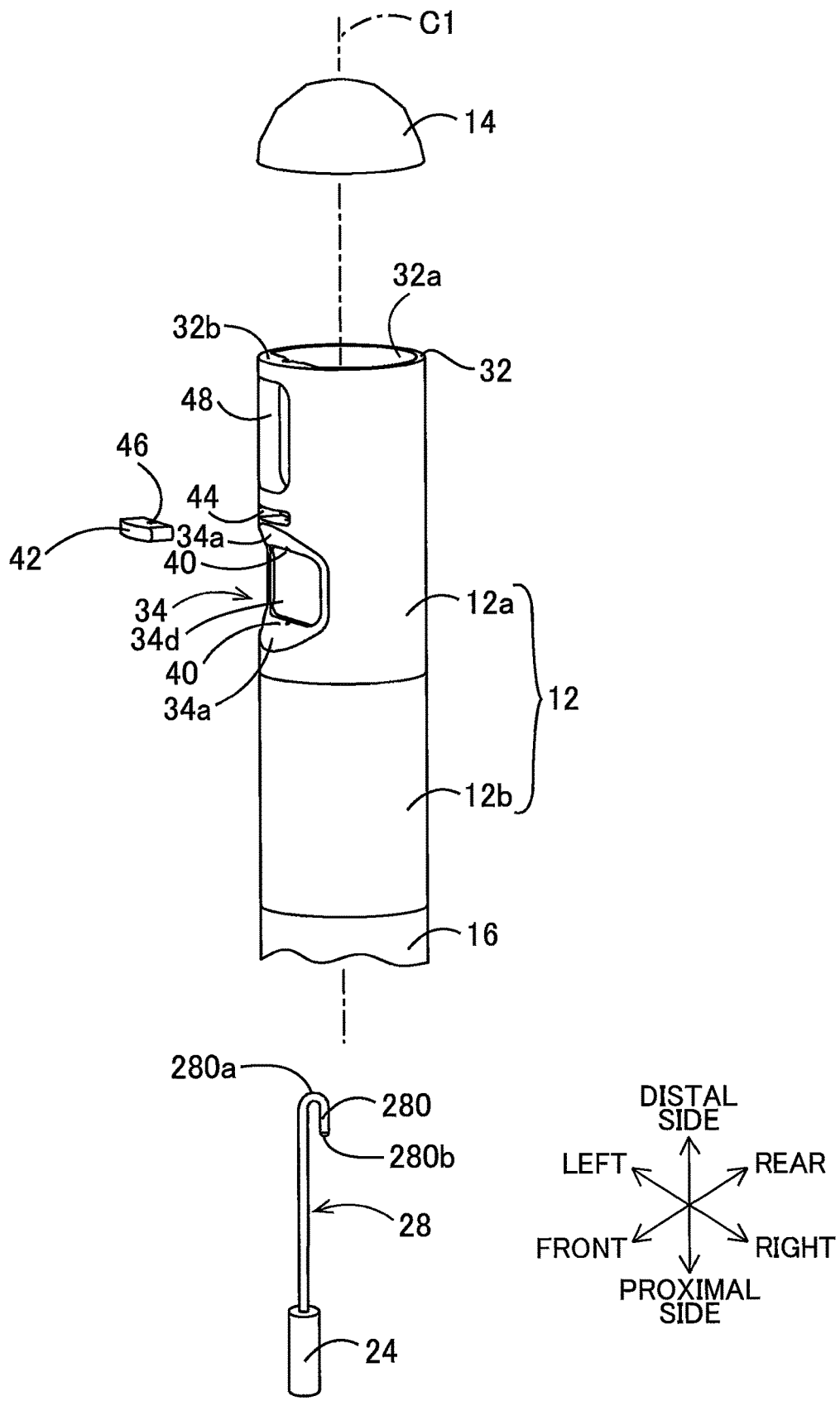
FIG. 4 is an exploded perspective view illustrating each component positioned in a cylindrical member in the suturing device according to the embodiment.
Figure 5:
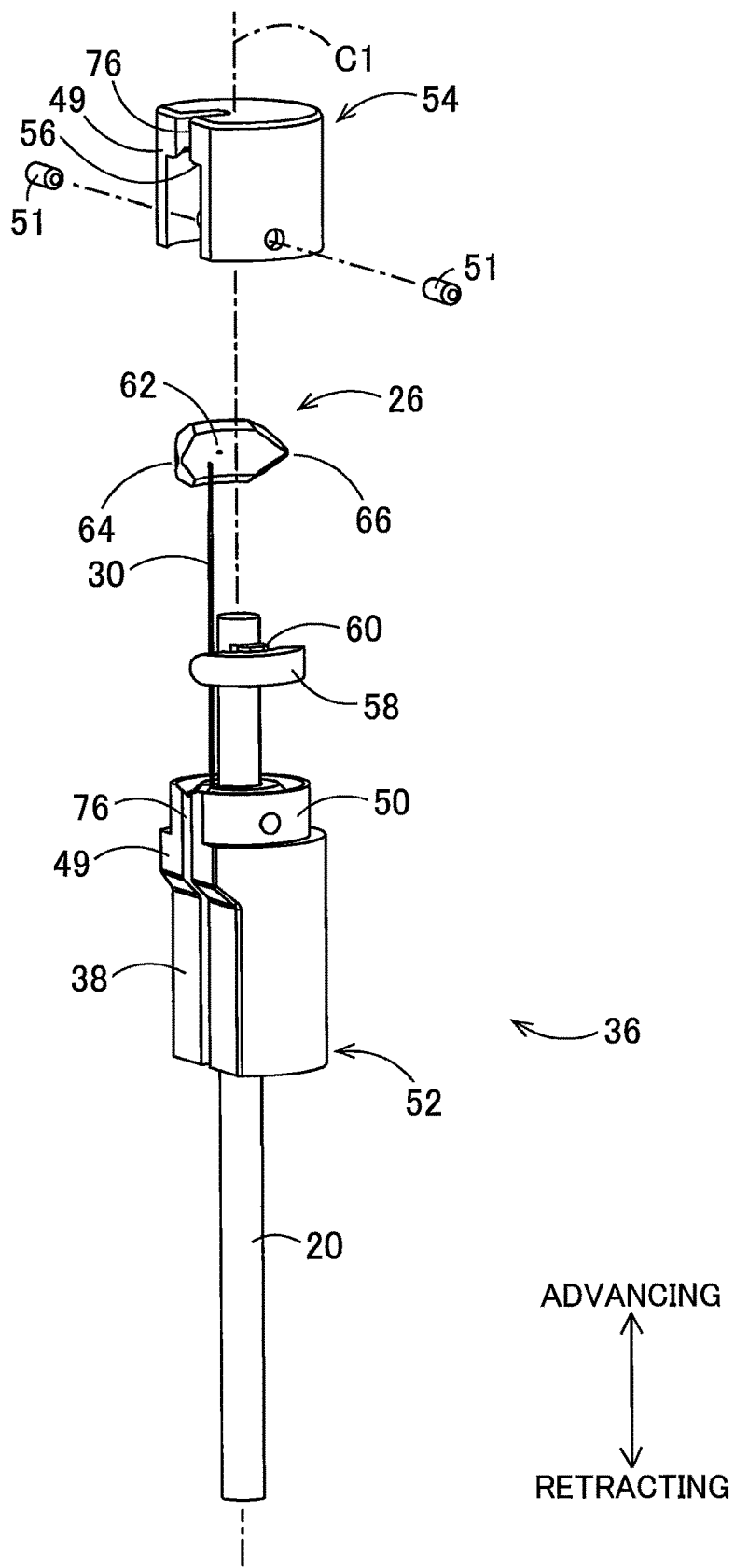
FIG. 5 is an exploded perspective view illustrating a shuttle guide member to be inserted in the cylindrical member in the suturing device according to the embodiment.
Figure 6:
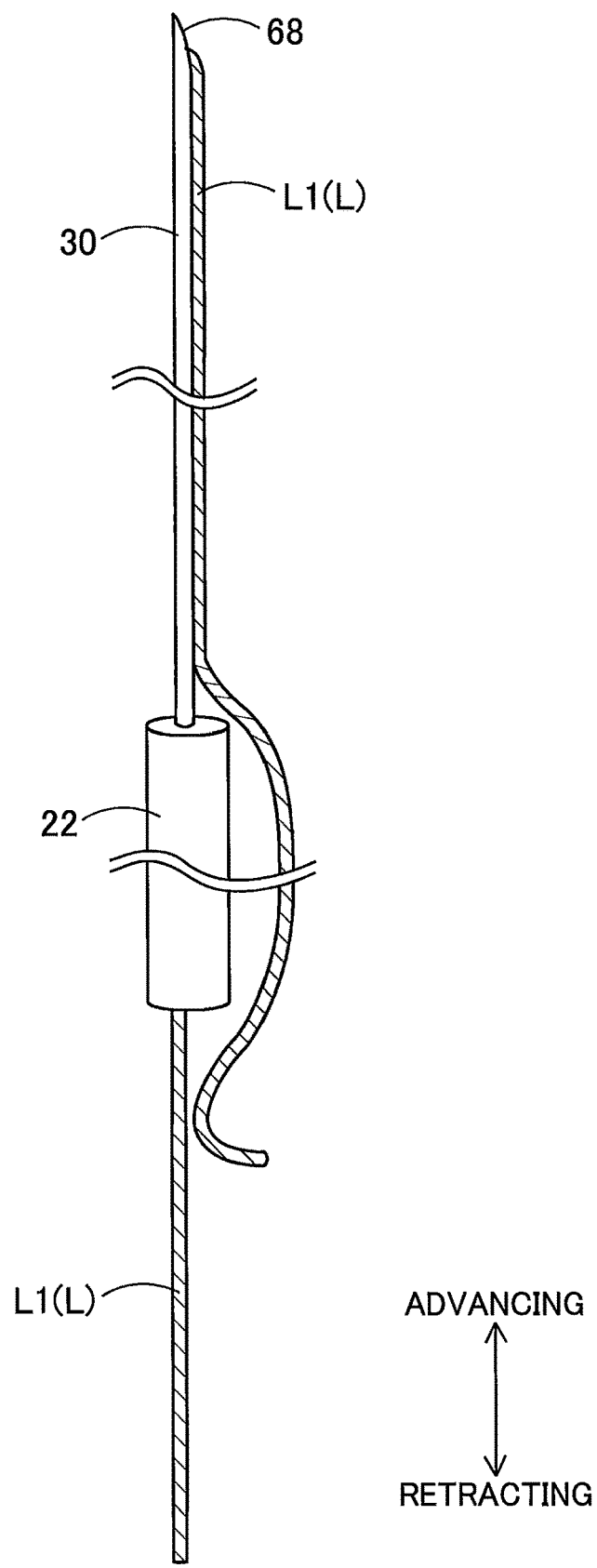
FIG. 6 is a perspective view illustrating one example of a needle to be inserted in the cylindrical member in the suturing device according to the embodiment.

FIG. 1 is a perspective view illustrating an entire exterior of a suturing device 10 according to one embodiment of the present disclosure. FIG. 2 is an enlarged perspective view illustrating a distal end portion of the suturing device 10. FIG. 3 is a right side view of the distal end portion of the suturing device 10 illustrated in FIG. 2. FIGS. 4, 5, and 6 illustrate the various components of the suturing device 10 in various disassembled states. In the present embodiment, the upper portion of the suturing device 10 in FIG. 1 will be called the distal end portion, and the bottom portion in FIG. 1 the proximal end portion.

The suturing device 10 has a long and hollow cylindrical member 12 that is closed on the distal end. The cylindrical member 12 functions as a casing. The cylindrical member 12 is formed of two interconnected cylindrical tubes 12a and 12b having an outer diameter of several millimeters, for example. A semispherical cap 14 is fitted onto the distal end of the cylindrical member 12 (the cylindrical tube 12a) for closing the opening in the distal end. In use, the proximal end of the cylindrical member 12 is coupled to the distal end of a tubular coupling member 16 that is flexible like a catheter, for example. The cylindrical member 12 and the semispherical cap 14 fitted on the distal end of the cylindrical member 12 function as the casing of the suturing device 10.

The suturing device 10 is provided with a first operating shaft 20, a second operating shaft 22, and a third operating shaft 24 that extend out from the proximal end of the cylindrical member 12 (the cylindrical tube 12b). The first operating shaft 20, second operating shaft 22, and third operating shaft 24 are flexible and serve to implement linear moving operations along the longitudinal direction of the cylindrical member 12 and rotating operations about respective axes.

The suturing device 10 is also provided with a first operating handle 21, a second operating handle 23, and a third operating handle 25 that are fixed to the proximal ends of the first operating shaft 20, second operating shaft 22, and third operating shaft 24, respectively. The first operating shaft 20 is a shuttle operating shaft for operating a shuttle 26 provided in the cylindrical member 12. The first operating handle 21 fixed to the proximal end of the first operating shaft 20 is used to remotely control the linear position of the shuttle 26 in the longitudinal direction of the cylindrical member 12 and the rotated position of the shuttle 26 about the axis of the first operating shaft 20. The second operating shaft 22 is a needle operating shaft for operating a needle 30 provided in the cylindrical member 12. The second operating handle 23 fixed to the proximal end of the second operating shaft 22 is used to remotely control the linear position of the needle 30 in the longitudinal direction of the cylindrical member 12 and the rotated position of the needle 30 about the axis of the second operating shaft 22. The third operating shaft 24 is a hook operating shaft that operates a hook member 28 provided in the cylindrical member 12. The third operating handle 25 fixed to the proximal end of the third operating shaft 24 is used to remotely control the linear position of the hook member 28 in the longitudinal direction of the cylindrical member 12 and the rotated position of the hook member 28 about the axis of the third operating shaft 24.

Arrows X in FIG. 1 illustrating rotating directions of the first operating handle 21, second operating handle 23, and third operating handle 25 indicate right-hand rotations. In the present embodiment described below, the state of the suturing device 10 illustrated in FIG. 1 will be considered a reference position, the side of s the suturing device 10 on the left diagonally near side of the drawing in FIG. 1 will be called the front side, the side of the suturing device 10 on the right diagonally far side of the drawing in FIG. 1 will be called the rear side. Further, the side of the suturing device 10 on the right diagonally near side of the drawing in FIG. 1 will be called the right side, and the side of the suturing device 10 on the left diagonally far side of the drawing in FIG. 1 will be called the left side. Furthermore, the clockwise rotation of the suturing device 10 when viewing the suturing device 10 along the longitudinal direction of the cylindrical member 12 from the proximal end toward the distal end will be called the clockwise rotation (CWR) or the right-hand rotation, and the counterclockwise rotation in the same view will be called the counterclockwise rotation (CCW) or the left-hand rotation.

As illustrated in FIG. 4, the cylindrical member 12 is configured of a circumferential wall 32 having an inner wall surface 32a. One portion of the circumferential wall 32 in the circumferential direction thereof is configured of a thick wall part 32b formed thicker than the other portions of the circumferential wall 32 having a uniform thickness. The thick wall part 32b is provided continuously along the longitudinal direction of the cylindrical member 12. The inner wall surface 32a is flat along the inside of the thick wall part 32b. In the present embodiment, the circumferential direction of the cylindrical member 12 denotes a direction around a center axis C1 of the cylindrical member 12.

A depression 34 is locally formed in one part of the cylindrical member 12 along the longitudinal direction of the same. The depression 34 is cut out from the circumferential wall 32 of the cylindrical member 12 (the cylindrical tube 12a) so as to form a recess in a portion of the cylindrical member 12 corresponding to the position of the thick wall part 32b. The depression 34 penetrates the thick wall part 32b of the cylindrical member 12 in the thickness direction thereof (i.e., the front-rear direction which is the direction orthogonal to the left-right direction and the longitudinal direction of the cylindrical member 12, hereinafter also called depthwise direction of the depression 34) and opens to expose the inside of the cylindrical member 12 to the outside thereof. The depression 34 is provided with a pair of sloped surfaces 34a that slope from the inner wall surface 32a toward the outer wall surface of the cylindrical member 12 on the distal side and proximal side of an opening 34d formed in the depression 34. As will be described later in FIG. 5, a shuttle guide member 36 is inserted in the distal end portion of the cylindrical member 12. When the shuttle guide member 36 is fitted into the cylindrical member 12, a first flat surface 38 formed on an outer circumferential surface of the shuttle guide member 36 closes the opening 34d of the depression 34.

As illustrated in FIGS. 2, 3, and 4, a needle guide groove 40 is formed in the thick wall part 32b of the cylindrical member 12 for guiding the needle 30 in the longitudinal direction of the cylindrical member 12, i.e., in a direction parallel to the center axis C1 of the cylindrical member 12. Through the needle guide groove 40, the needle 30 moves along a path K parallel to the center axis C1 of the cylindrical member 12. The needle 30 is reciprocated in the longitudinal direction of the cylindrical member 12 between an advanced end position (the position farthest toward the distal end of the cylindrical member 12) and a retracted end position (the position farthest toward the proximal end of the cylindrical member 12) with a stroke longer than the opening dimension Lo of the depression 34 in the longitudinal direction of the cylindrical member 12. The opening dimension Lo is the length of a straight line leading from the intersecting point between the path K of the needle 30 and the proximal side of the depression 34 (i.e., a proximal edge 34b of the opening 34d of the depression 34) to the intersecting point between the path K of the needle 30 and the distal side of the depression 34 (i.e., a distal edge 34c of the opening 34d of the depression 34). Alternatively, the needle 30 may be reciprocated in the longitudinal direction of the cylindrical member 12 at a stroke longer than the longitudinal opening dimension Lo of the opening 34d that penetrates the thick wall part 32b of the cylindrical member 12 in the thickness direction thereof to expose a part of the path K of the needle 30 to the outside of the cylindrical member 12.

In the present embodiment, movement of the needle 30 will be called "advancing" when the needle 30 advances toward the distal side of the cylindrical member 12 and "retracting" when the needle 30 is retracted toward the proximal side of the cylindrical member 12. The distal end of the needle 30 is at the advanced end A of the path K when the needle 30 is in the advanced end position, and is at the retracted end B of the path K when the needle 30 is in the retracted end position. Since the retracted end B of the path K is closer to the proximal end of the cylindrical member 12 than the proximal edge 34b of the depression 34, the needle 30 is not exposed in the depression 34 when the needle 30 is in the retracted end position. However, the needle 30 is exposed in the depression 34 when the needle 30 is in the advanced end position since the distal end of the needle 30 is at the advanced end A of the path K which is closer to the distal end of the cylindrical member 12 than the distal edge 34c of the depression 34, and the proximal end of the needle 30 is at a position closer to the proximal end of the cylindrical member 12 than the proximal edge 34b of the depression 34.

FIG. 2 illustrates the state of the needle 30 in the advanced end position. The path K of the distal end of the needle 30 extending from the retracted end B to the advanced end A passes through the depression 34 in the longitudinal direction of the cylindrical member 12, and the needle groove 40 is in communication with the depression 34 through the sloped surfaces 34a. The sloped surfaces 34a are parts of the thick wall part 32b. Here, the outer wall surface of the depression 34 is configured by the sloped surfaces 34a and the first flat surface 38. Note that the longitudinal dimension Lh of the depression 34 in the longitudinal direction of the cylindrical member 12 is greater than the depthwise dimension D of the depression 34 in the depthwise direction of the depression 34 which is the direction orthogonal to the longitudinal direction of the cylindrical member 12 (i.e., front-rear direction in the present embodiment, and the left-right direction of the drawing in FIG. 3).

The shortest distance in the depthwise direction of the depression 34 between the outer wall surface of the depression 34 and the path K of the distal end of the needle 30 changes either continuously or intermittently along the direction in which the needle 30 moves. That is, in a plane that includes the path K for the distal end of the needle 30 and the center axis C1 of the cylindrical member 12, the distance in the depthwise direction of the depression 34 between the needle 30 in the advanced end position and the first flat surface 38 formed on a shuttle guide main body 52 (described later) is constant along the moving direction of the needle 30. The distance in the depthwise direction of the depression 34 changes uniformly between the needle 30 and the sloped surfaces 34a sloped relative to the first flat surface 38. The first flat surface 38 has a function for positioning biological tissue T received in the depression 34 as a suturing target. The position of the needle 30 relative to the first flat surface 38 is preset to achieve a target piercing position for the needle 30 relative to the thickness direction of the wall forming the biological tissue T. The needle guide groove 40 is formed in both the distal side of the depression 34 and the proximal side of the depression 34 in order to position the needle 30 at the target piercing position. In the present embodiment, the distance between the first flat surface 38 and needle 30 is set so that the needle 30 passes through the wall forming the biological tissue T.

Figure 7:
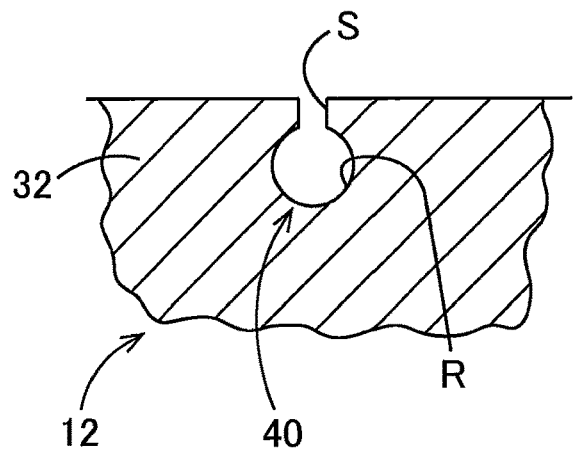
FIG. 7 is an enlarged cross-sectional view of a needle guide groove formed in a circumferential wall of the cylindrical member in the suturing device according to the embodiment.

As illustrated in the enlarged view of FIG. 7, a cross section of the needle guide groove 40 forms a circle R having a diameter equivalent to the outer dimension of the needle 30 in order to allow passage of the needle 30. Part of the circle R is in communication with the flat inner wall surface 32a on the thick wall part 32b via a slit S having a width dimension smaller than the diameter of the needle guide groove 40.

As illustrated in FIG. 4, a fitting groove 44 is formed in the cylindrical member 12 at a position on the distal side of the depression 34. A friction member 32 formed of silicone rubber or the like is fitted into the fitting groove 44. The friction member 42 is fitted into the fitting groove 44 so as to contact the outer surface of the needle 30 when the needle 30 has advanced passed the depression 34 of the cylindrical member 12 toward the advanced end position. A notched groove 46 is formed in the friction member 42 at a position for receiving insertion of the needle 30. The notched groove 46 has the same cross-sectional shape as the needle guide groove 40. This friction member 42 applies friction resistance to a first portion of a thread-like member L (hereinafter called first thread-like member L1) that extends out from the distal end portion of the needle 30, as illustrated in FIG. 6, when the needle 30 is retracted a prescribed amount such that its distal end moves along the path K from the advanced end A toward the retracted end B of the path K, easily forming a loop LP with a semicircular shape by causing the first thread-like member L1 to separate from the distal end portion of the needle 30. However, the friction member 42 is not absolutely necessary, provided that the loop LP can be formed through friction generated between the needle guide groove 40 and the first thread-like member L1 extending from the distal end portion of the needle 30 when the needle 30 is retracted along the path K the prescribed amount such that the distal end of the needle 30 moves from the advanced end A toward the retracted end B of the path K. Alternatively, the loop LP may be formed through flexural rigidity of the thread-like member L itself.

In the present embodiment, a penetrating hole 48 penetrating the circumferential wall 32 of the cylindrical member 12 is provided between the depression 34 of the cylindrical member 12 and the semispherical cap 14 in the longitudinal direction of the cylindrical member 12 for confirming the operations of the shuttle 26 and the like. However, the penetrating hole 48 does not contribute to the function of the suturing device 10 for forming stitches or knots and therefore is not essential.

The shuttle guide member 36 illustrated in FIG. 5 is a columnar member that shares the center axis C1 of the cylindrical member 12 as its own center axis. The shuttle guide member 36 has an outer circumferential surface formed with the same cross-sectional shape as the inner wall surface 32a, which constitutes the inner surface of the circumferential wall 32 of the cylindrical member 12. When fitted into the cylindrical member 12, the shuttle guide member 36 is capable of moving in the longitudinal direction within the cylindrical member 12 but is incapable of rotating relative to the cylindrical member 12 about the center axis C1. As illustrated in FIG. 5, the shuttle guide member 36 has a second flat surface 49 parallel to the center axis C1 on a portion of its outer surface, forming an outer circumferential surface that is D-shaped in cross section and similar in shape to the inner wall surface 32a of the cylindrical member 12. The plane passing through the second flat surface 49 is parallel to the plane passing through the first flat surface 38, and the second flat surface 49 is separated farther than the first flat surface 38 from the center axis C1.

As illustrated in detail in FIG. 5, the shuttle guide member 36 is provided with the shuttle guide main body 52, and a shuttle guide pressing member 54. The shuttle guide main body 52 has a small-diameter fitting part 50 that protrudes toward the distal end of the cylindrical member 12. The shuttle guide pressing member 54 is fixed to the shuttle guide main body 52 by securing pins 51 while the shuttle guide pressing member 54 is fitted over the small-diameter fitting part 50. An annular shuttle guide groove 56 is defined between the shuttle guide main body 52 and shuttle guide pressing member 54 for guiding the shuttle 26 in a circumferential direction which is a direction around the center axis C1. The shuttle guide groove 56 may be formed in the inner wall of the shuttle guide pressing member 54 following the circumferential direction along the outer circumference of the shuttle 26.

The advanced end portion of the first operating shaft 20 passes through the shuttle guide main body 52, and the first operating shaft 20 is capable of rotating relative to the shuttle guide main body 52 about the center axis C1. An arm 60 extends radially outward from the center axis C1 toward the inner wall surface 32a of the circumferential wall 32 of the cylindrical member 12 on the advanced end portion of the first operating shaft 20. An arcuate pusher 58 is fixed to the aim 60 for contacting a circumferential end of the shuttle 26 in order to move the shuttle 26 in the circumferential direction. The pusher 58 has an arcuate shape and a circumferential length that corresponds to an angle less than 180 degrees, such as approximately 160 degrees, whose vertex is the center axis C1 of the shuttle guide member 36.

The shuttle 26 has an arcuate shape and a circumferential length that corresponds to an angle less than 180 degrees, such as approximately 160 degrees, whose vertex is the center axis C1 of the columnar shuttle guide member 36 in which is formed the shuttle guide groove 56 for guiding the shuttle 26. A holding part 62 is formed in the circumferential center portion of the shuttle 26. The holding part 62 is configured of a through-hole that holds the second thread-like member L2 a second portion of the thread-like member L (hereinafter called second thread-like member L2) depicted by a dashed line in FIG. 11 by passing the second tread-like member L2 through the holding part 62. In the present embodiment, the thread-like member L is a single thread in which the first portion (first thread-like member L1) is continuous with the second portion (second thread-like member L2). The thread-like member L may be configured of two thread-like members including a first thread-like member L1 and a second thread-like member L2. Both circumferential ends of the shuttle 26 taper away from the holding part 62 to form a first hook-shaped end 64 and a second hook-shaped end 66, respectively, formed with sharp angled tips.

As illustrated in FIG. 6, the proximal end of the needle 30 is coupled with the second operating shaft 22, and the needle 30 is guided in the longitudinal direction of the cylindrical member 12 along the center axis C1 by the needle guide groove 40 formed in the cylindrical member 12. A distal opening 68 is formed in the distal end of the needle 30. The first thread-like member L1 inserted through the inside of the second operating shaft 22 and needle 30 is guided out of the needle 30 through the distal opening 68.

The needle guide groove 40 formed in the cylindrical member 12 is positioned such that the path K of the distal end of the needle 30 passes through the space inside the depression 34. When an operation performed with the second operating handle 23 in a direction toward the distal side or the proximal side of the cylindrical member 12 in the longitudinal direction thereof is transmitted via the second operating shaft 22, the needle 30 is advanced or retracted along the path K. Further, when an operation performed on the second operating handle 23 for rotating about the axis of the second operating shaft 22 is transmitted via the second operating shaft 22, the needle 30 is rotated about its axis, wrapping the first thread-like member L1 about the circumference of the needle 30.

As illustrated by the dashed line in FIG. 3, for example, the path K described above is set inside the cylindrical member 12 to a range in the longitudinal direction of the cylindrical member 12 between the advanced end A positioned near the distal end of the cylindrical member 12 and the retracted end B positioned a prescribed distance into the proximal side of the cylindrical member 12 from the proximal edge 34b of the opening 34d of the depression 34. This distance between the advanced end A and retracted end B denotes the stroke of the distal end of the needle 30. That is, the advanced end A and retracted end B correspond to stroke ends of the distal end of the needle 30.

Figure 8:
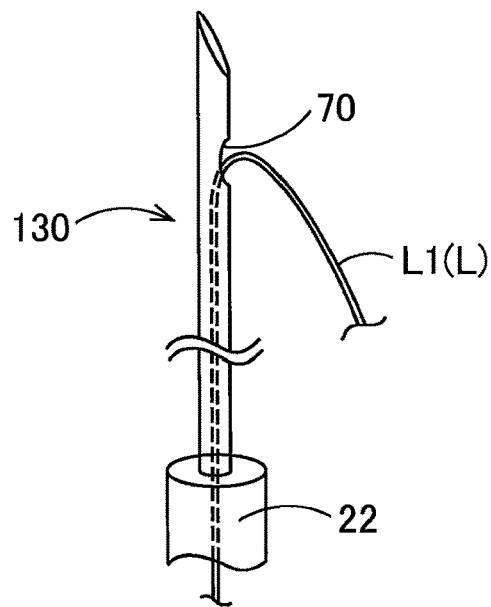
FIG. 8 is a perspective view illustrating another example of a needle having a shape different from the shape of the needle illustrated in FIG. 6.
Figure 9:
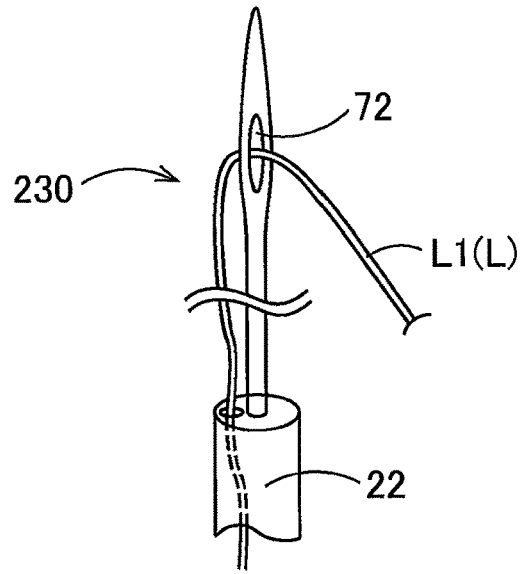
FIG. 9 is a perspective view illustrating still another example of a needle having a shape different from the shape of the needle illustrated in FIG. 6.

The needle 30 is configured of a thin hollow tube having a cylindrical shape that is similar in shape to a hypodermic needle, for example. As an alternative of the needle 30, as illustrated in FIG. 8, a needle 130 having an opening 70 formed in the peripheral wall near the distal end thereof in place of the distal opening 68 may be used. With this configuration, the first thread-like member L1 is exposed from the opening 70. As another alternative of the needle 30, as illustrated in FIG. 9, a needle 230 having a thread hole 72 formed near the distal end thereof in place of the distal opening 68 may be used. With this configuration as well, the first portion thread-like member L1 can be anchored in the thread hole 72.

Figure 10:
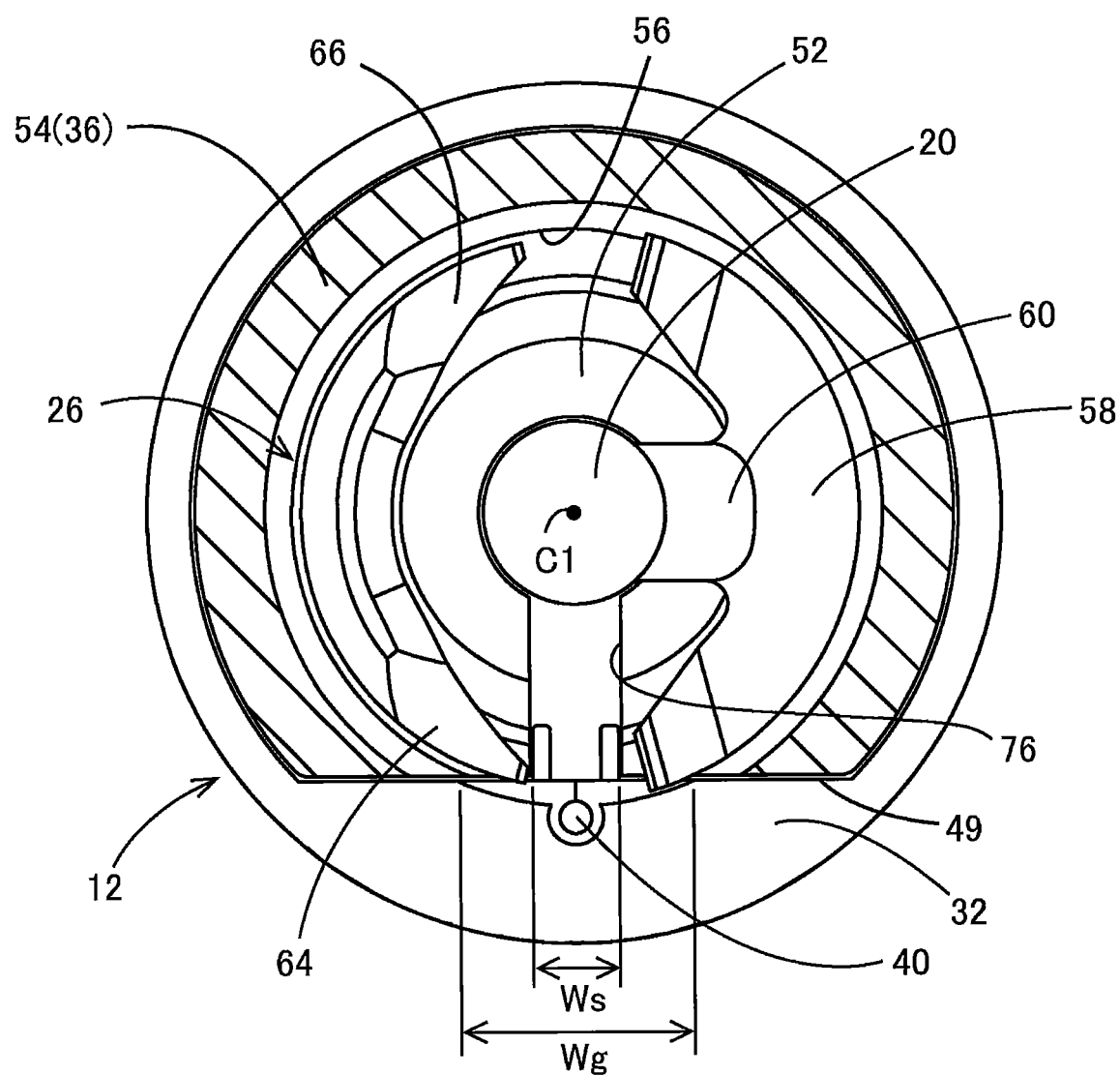
FIG. 10 is a view illustrating a distal end face of the cylindrical member from which a semispherical cap is removed and a cross section of the shuttle guide member taken along a plane passing through a shuttle guide groove in the suturing device according to the embodiment.

FIG. 10 illustrates the distal end face of the cylindrical member 12 after the semispherical cap 14 has been removed, and a cross section of the shuttle guide member 36 inside the cylindrical member 12 taken along a plane passing through the annular shuttle guide groove 56. In other words, the drawing illustrates the shuttle guide member 36 depicted in a cross section taken through a plane orthogonal to the center axis C1 and passing through the shuttle guide groove 56 as viewed inside the cylindrical member 12 from the distal end face with the semispherical cap 14 removed. As illustrated in FIG. 10, the shuttle guide groove 56 is open in the second flat surface 49 and has an opening width Wg that is larger than the width dimension Ws of a slit 76 illustrated in FIG. 5. Note that the first thread-like member L1 and second thread-like member L2 have been omitted from FIG. 10.

The slit 76 is formed in the portion of the shuttle guide member 36 positioned on the center axis C1 side of the needle guide groove 40. As described above, the loop LP is formed in the first thread-like member L1 extending out of the distal end of the needle 30 when the needle 30 is retracted a prescribed distance along the path K in the direction from the advanced end A of the path K toward the retracted end B of the path K. The slit 76 configures a loop support space for accommodating the shape of the loop LP and for maintaining the shape of the loop LP. The slit 76 is formed at a length in the longitudinal direction of the path K and a depth in the radial direction of the shuttle guide member 36 reaching to the first operating shaft 20. The slit 76 in the present embodiment is formed at the same length as the path K through the shuttle guide main body 52 and the shuttle guide pressing member 54 and at a depth that reaches the outer circumferential surface of the first operating shaft 20.

The slit 76 extending in the longitudinal direction of the cylindrical member 12 and the annular shuttle guide groove 56 extending in the circumferential direction of the cylindrical member 12 intersect each other and are in communication with each other. The diameter of the annular shuttle guide groove 56 from groove bottom to groove bottom via the center axis C1 is set larger than the twice the distance between the second flat surface 49 and center axis C1 and is set to a diameter that passes approximately through the outer radial surface of the path K for the needle 30 guided by the needle guide groove 40. Consequently, part of the circular path followed by the shuttle 26 that is guided by the shuttle guide groove 56 protrudes radially outward from the second flat surface 49 formed on the shuttle guide main body 52 and shuttle guide pressing member 54.

When a rotating operation performed on the first operating handle 21 is transmitted through the first operating shaft 20, the arcuate pusher 58 is rotated about the center axis C1 in a circumferential direction, contacts one circumferential end of the shuttle 26, and moves the shuttle 26 in the circumferential direction along the shuttle guide groove 56. When the first operating handle 21 is operated toward the distal end or proximal end of the cylindrical member 12 along the longitudinal direction of the same, this operation is transmitted to the shuttle guide member 36 via the first operating shaft 20. Consequently, the shuttle guide member 36 is moved relative to the cylindrical member 12 toward the distal side or proximal side in the longitudinal direction of the cylindrical member 12. At the same time, the shuttle 26 is pushed by the shuttle guide main body 52 or shuttle guide pressing member 54 and is similarly moved relative to the needle 30 in the cylindrical member 12 toward the distal side or proximal side of the cylindrical member 12 along the longitudinal direction of the same.

FIGS. 11 through 15 are drawings illustrating the same view as that in FIG. 10 to describe the sequential operations for passing the shuttle 26 through the loop LP formed inside the slit 76 by the first thread-like member L1 extending from the distal end portion of the needle 30 through a rotating operation on the first operating handle 21. FIGS. 11 through 15 illustrate the shuttle 26 from the distal side of the cylindrical member 12 in the longitudinal direction.

Figure 11:
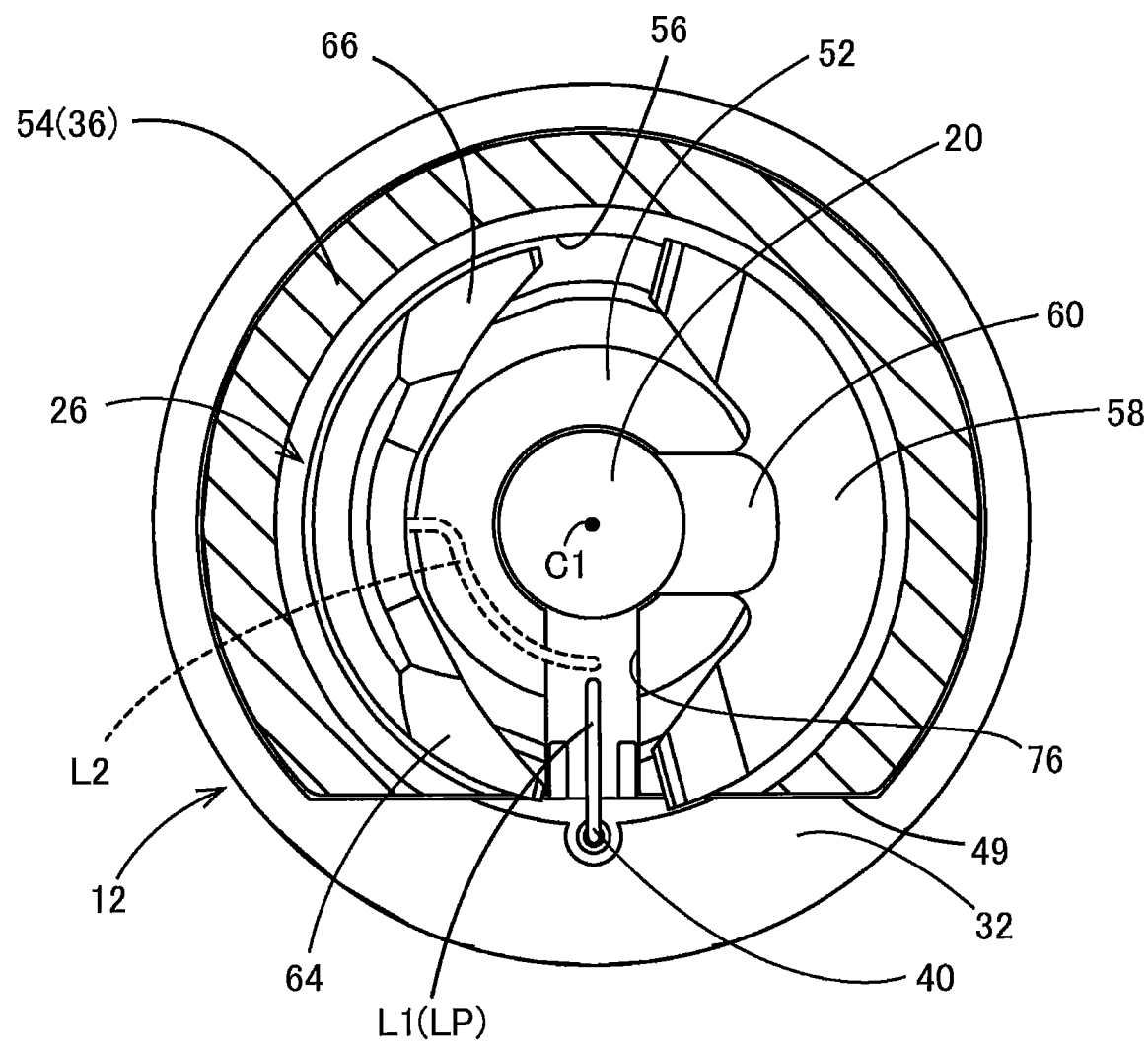
FIG. 11 is a view corresponding to FIG. 10 and illustrating an initial state of the suturing device according to the embodiment in which a loop is formed in a first thread-like member extending from a distal end of the needle of FIG. 6.

FIG. 11 illustrates an initial state in which the loop LP is formed in the first thread-like member L1 extending from the distal end portion of the needle 30 when the needle 30 is retracted the prescribed distance along the path K in a direction from the advanced end A toward the retracted end B of the path K. The second thread-like member L2 is held in the shuttle 26. In the initial state illustrated in FIG. 11, the shuttle 26 is in a left stop position, and the pusher 58 is in a right stop position. In this state, when the pusher 58 is rotated about the center axis C1 through a right-hand rotating operation performed on the first operating handle 21, the pusher 58 contacts the second hook-shaped end 66 of the shuttle 26 and moves the shuttle 26 in the circumferential direction along the shuttle guide groove 56.

Figure 12:
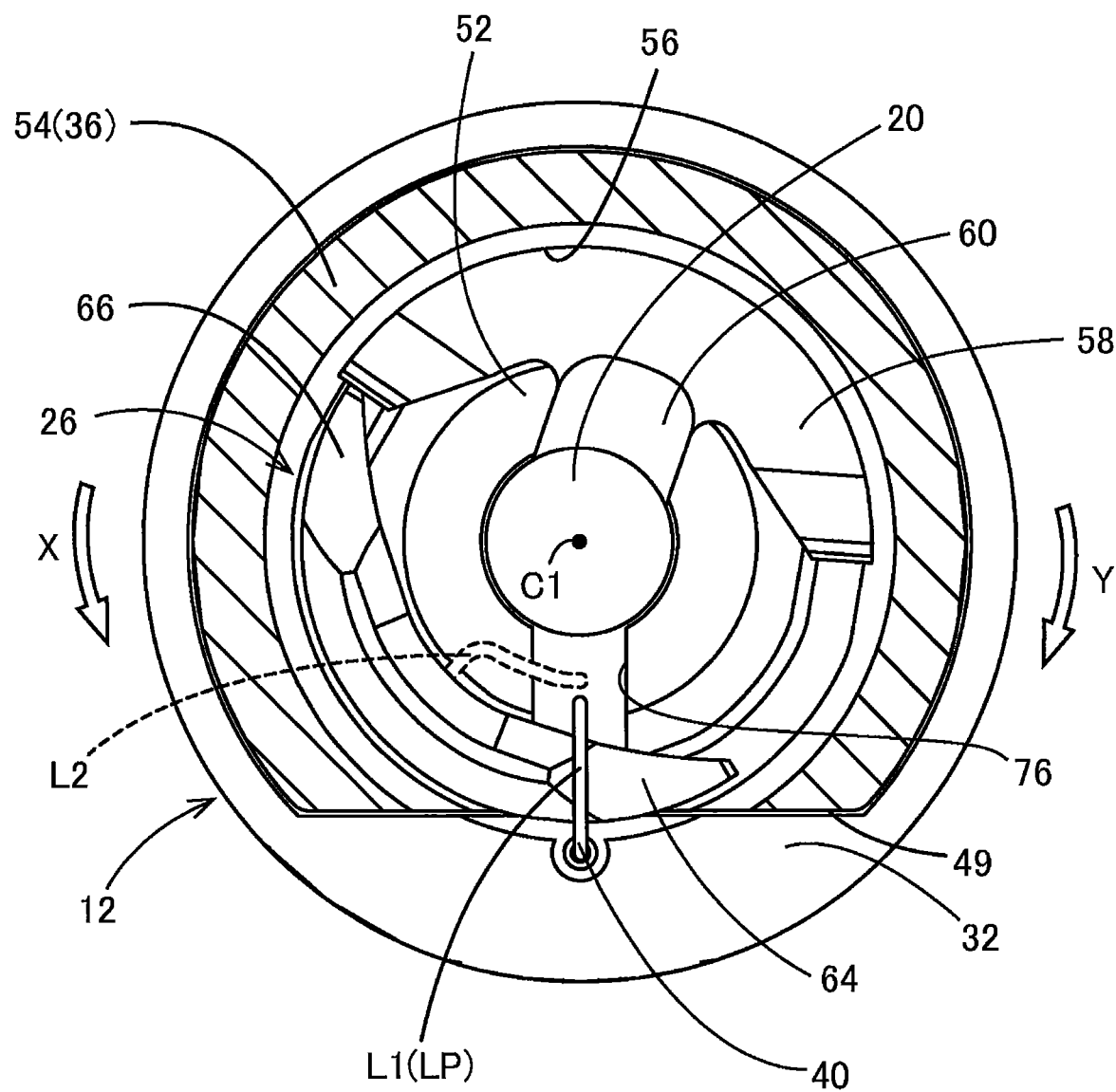
FIG. 12 is a view corresponding to FIG. 10 and illustrating a state of the suturing device according to the embodiment after a right-hand rotating operation of approximately 70 degrees has been performed with a first operating handle, whereby a first hook-shaped end of a shuttle has passed through the loop.
Figure 13:
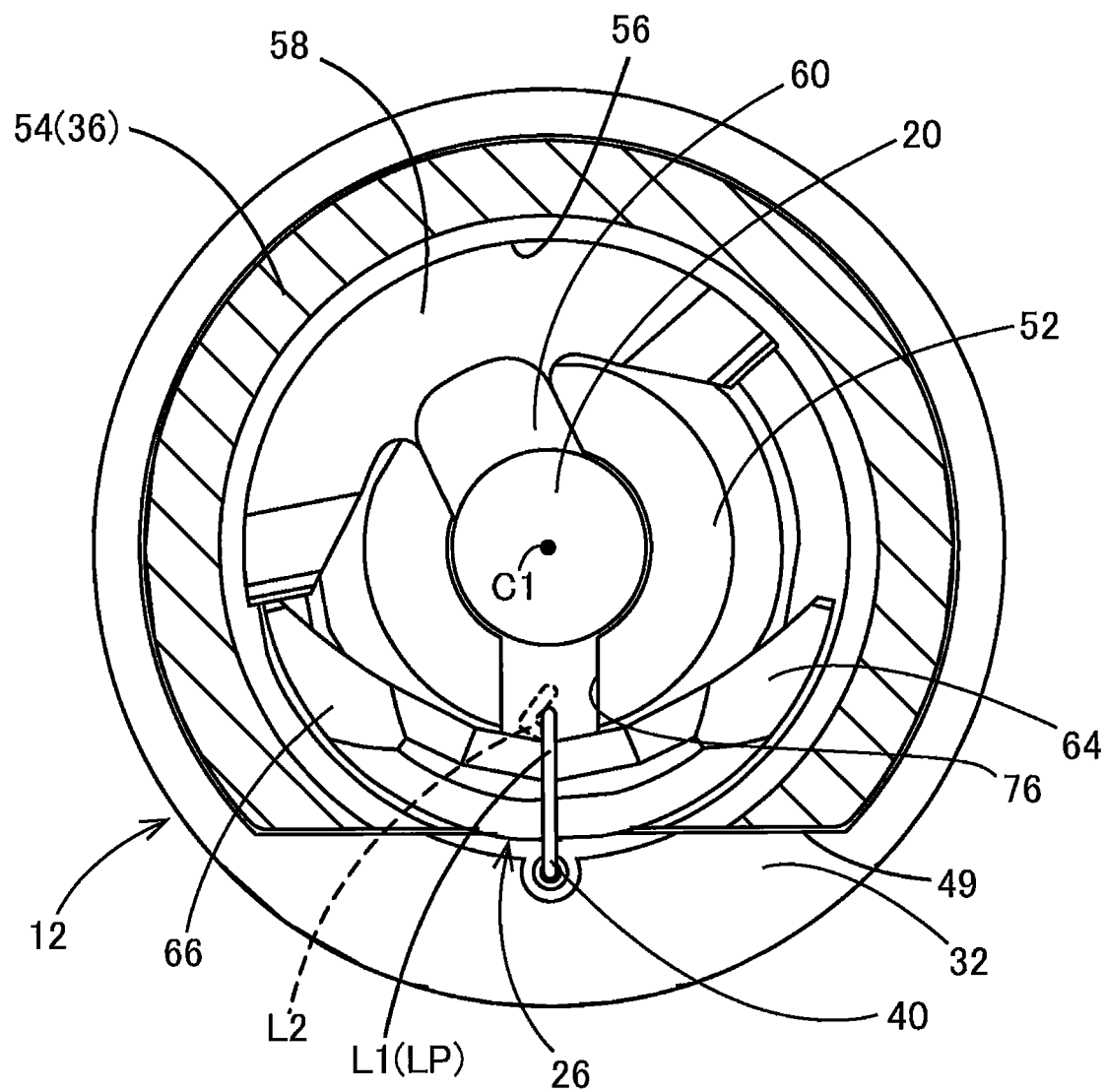
FIG. 13 is a view corresponding to FIG. 10 and illustrating a state of the suturing device according to the embodiment after a right-hand rotating operation of approximately 110 degrees has been performed with the first operating handle, whereby a circumferential center portion of the shuttle has become positioned inside the loop.
Figure 14:
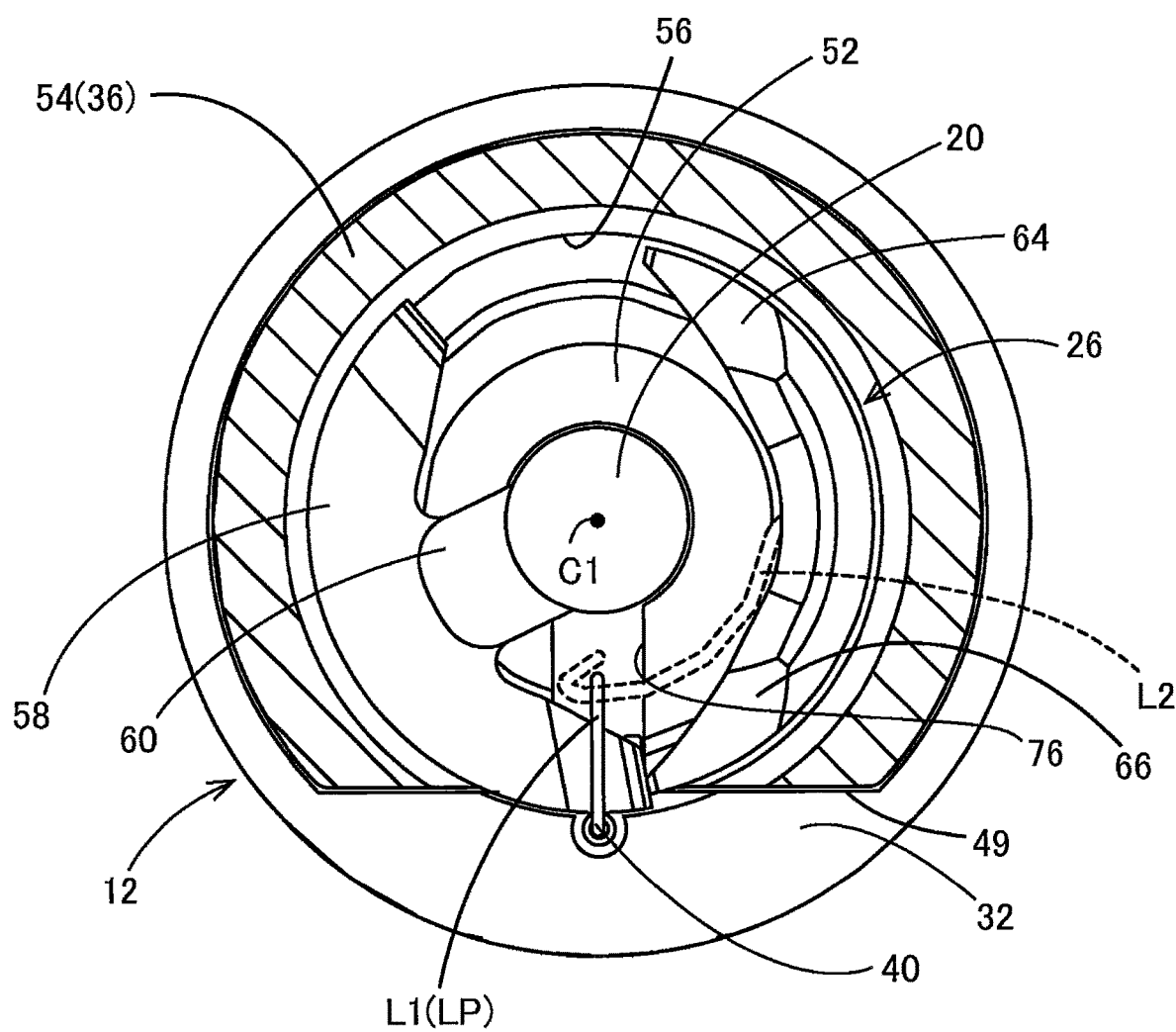
FIG. 14 is a view corresponding to FIG. 10 and illustrating a state of the suturing device according to the embodiment after a right-hand rotating operation of approximately 200 degrees has been performed with the first operating handle, whereby the entire shuttle has passed through the loop and an end of a pusher has become positioned inside the loop.

FIG. 12 illustrates a state after a right-hand rotating operation of approximately 70 degrees has been performed with the first operating handle 21, whereby the first hook-shaped end 64 of the shuttle 26 being moved in the X-direction has passed through the loop LP. The Y-direction indicates the moving direction of the shuttle during a left-hand rotating operation on the first operating handle 21. FIG. 13 illustrates a state after a right-hand rotating operation of approximately 110 degrees has been completed on the first operating handle 21, whereby the longitudinal (circumferential) center portion of the shuttle 26 has become positioned inside the loop LP. FIG. 14 illustrates a state after a right-hand rotating operation of approximately 200 degrees has been completed on the first operating handle 21, whereby the entire shuttle 26 has passed through the loop LP and an end of the pusher 58 has become positioned inside the loop LP. In a state illustrated in FIG. 14, the shuttle 26 is in a right stop position, and the pusher 58 is in a leftmost end position. Note that since the view in FIGS. 11 through 14 is from the distal side of the cylindrical member 12 in the longitudinal direction thereof, the movement of the shuttle 26 in the drawings is depicted as left-hand rotation.

Figure 15:
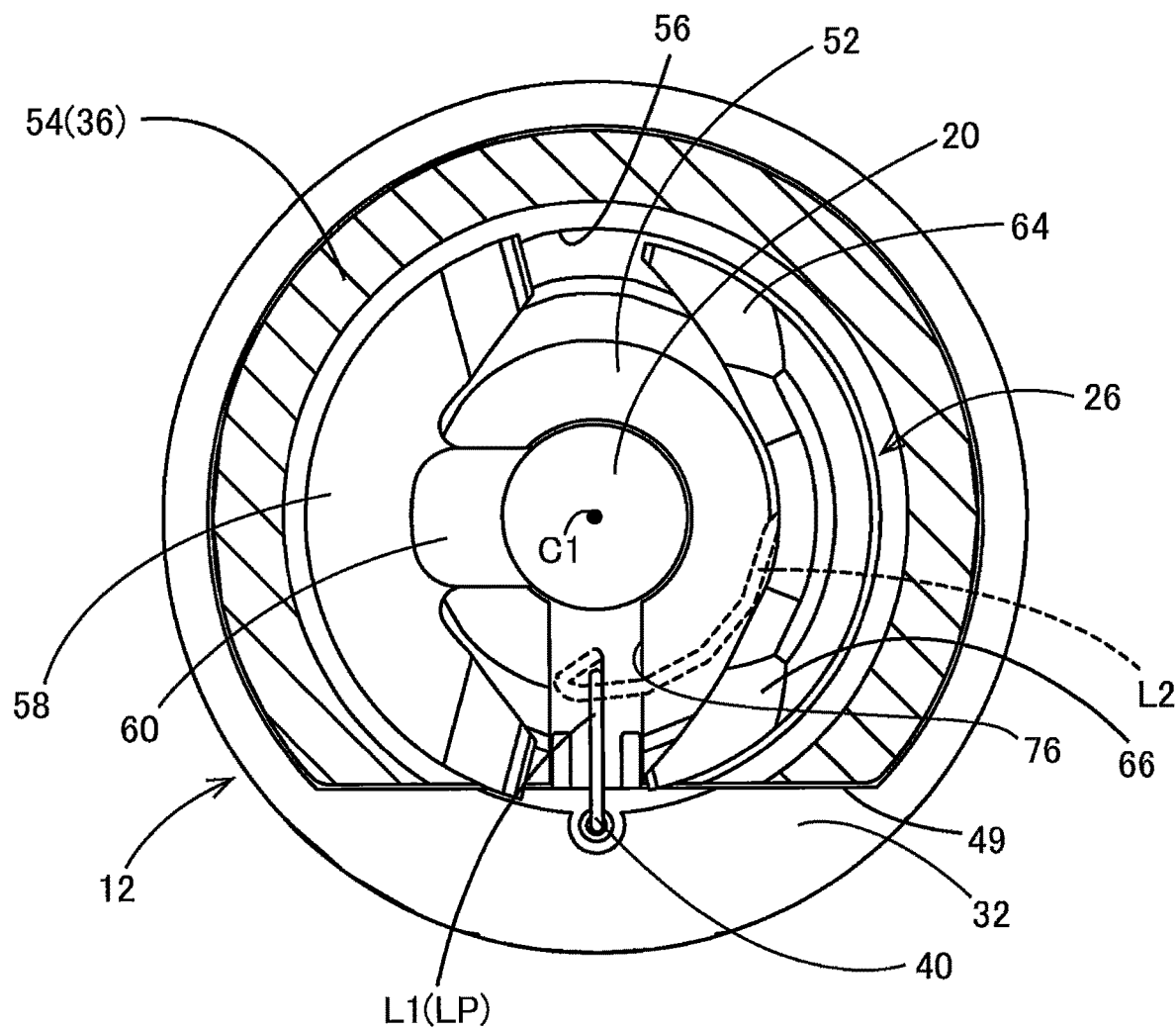
FIG. 15 is a view corresponding to FIG. 10 and illustrating a state of the suturing device according to the embodiment after a left-hand rotating operation of approximately 20 degrees has been performed with the first operating handle from the position illustrated in FIG. 14, whereby both the shuttle and pusher are in positions rotated in 180 degrees from the initial positions illustrated in FIG. 11.

FIG. 15 illustrates a state after performing a reverse rotating operation (i.e., a left-hand rotation) of approximately 20 degrees on the first operating handle from the position illustrated in FIG. 14. Through this left-hand rotation, the shuttle 26 and the pusher 58 is pivotally moved in the Y-direction until both the shuttle 26 and pusher 58 are in positions rotated 180 degrees from their initial positions illustrated in FIG. 11. In this state illustrated in FIG. 15, the shuttle 26 is in the right stop position, and the pusher 58 is in a left stop position.

Through these operations illustrated in FIGS. 11 to 15, the second thread-like member L2 held in the holding part 62 of the shuttle 26 is passed through the loop LP formed in the first thread-like member L1 at the distal end portion of the needle 30 so that the second thread-like member L2 intersects the loop LP in the first thread-like member L1.

As illustrated in FIG. 4, the hook member 28 in the cylindrical member 12 has a hook part 280 on its distal end portion that is curved into a hook shape, while the proximal end of the hook member 28 is coupled to the third operating shaft 24. When the rotating operation performed with the third operating handle 25 is transmitted through the third operating shaft 24, the hook member 28 rotates about its axis (axis of the third operating shaft 24) in the cylindrical member 12 and hooks or detaches from the first thread-like member L1 or second thread-like member L2 positioned between the needle 30 and shuttle 26. Further, when an operation on the third operating handle 25 toward the distal side of the cylindrical member 12 or proximal side of the cylindrical member 12 in the longitudinal direction is transmitted via the third operating shaft 24, the hook member 28 in the cylindrical member 12 forms slack or takes up slack in the first thread-like member L1 or second thread-like member L2 positioned between the needle 30 and shuttle 26.

In other words, the hook member 28 capable of hooking a thread-like member L positioned between the needle 30 and shuttle 26 in the cylindrical member 12 is provided so as to be movable in the longitudinal direction of the cylindrical member 12. Note that the hook member 28 may also possess a latch for opening and closing the opening in the hook part 280. Alternatively, the hook part 280 may be configured of a shape memory alloy, and the opening in the hook part 280 may be selectively opened and closed by raising or lowering the temperature. In this case, the hook member 28 can be more easily unhooked from a thread-like member by increasing the opening in the hook part 280.

A suturing target clamping mechanism 78 for placing the biological tissue T in contact with the depression 34 to immobilize the biological tissue T is provided in the cylindrical member 12. The biological tissue T constitutes the suturing target and may be the left atrial appendage that protrudes locally as a pouch from the wall of the left ventricle of the heart, for example. The suturing target clamping mechanism 78 is configured of a balloon (expanding bag) 78a disposed on the outer wall surface of the circumferential wall 32 of the cylindrical member 12.

For example, the suturing target clamping mechanism 78 may be disposed in an area of the cylindrical member 12 positioned on the opposite side of the center axis C1 from the depression 34, as illustrated in FIG. 3. In other words, in the suturing device 10 of the present embodiment, the depression 34 is formed in the front surface of the outer wall 32 of the cylindrical member 12, while the suturing target clamping mechanism 78 is disposed on the rear surface thereof.

The suturing target clamping mechanism 78 may be configured of a plurality of balloons or a plurality of other members. In other words, instead of a balloon formed of a resin material, the suturing target clamping mechanism 78 may be configured of a metallic member, provided that the suturing target clamping mechanism 78 can immobilize the biological tissue T. A hose (not illustrated) for supplying pressurized fluid to the suturing target clamping mechanism 78 is connected to the balloon 78a configuring the suturing target clamping mechanism 78.

Here, the positions of the shuttle 26 and needle 30 will be described using the expressions advanced end and retracted end, while the position of the hook member 28 will be described using the expressions advanced end, advanced, retracted, and retracted end.

Hereinafter, the shuttle 26 being in the retracted end position signifies that the shuttle 26 is positioned farther toward the retracted side in the longitudinal direction of the cylindrical member 12 than the proximal end of the cylindrical member 12. The shuttle 26 being in the advanced end position signifies that the shuttle 26 is positioned farther toward the distal side (advanced side) in the longitudinal direction of the cylindrical member 12 than the distal edge 34c of the depression 34 in the cylindrical member 12.

The needle 30 being in the advanced end position signifies that the distal end of the needle 30 is farther toward the distal side (advanced side) in the longitudinal direction of the cylindrical member 12 than the distal edge 34c of the opening 34d of the depression 34 in the cylindrical member 12 and farther toward the distal side (advanced side) of the cylindrical member 12 than the shuttle 26 positioned in the advanced end position. In the present embodiment, as described above, the needle 30 being in the advanced end position denotes that the distal end of the needle 30 is at the advanced end A of the path K illustrated in FIG. 3. The needle 30 being in the retracted end position denotes that the distal end of the needle 30 is positioned farther toward the proximal side (retracted side) in the longitudinal direction of the cylindrical member 12 than the proximal edge 34b of the opening 34d of the depression 34 in the cylindrical member 12. In the present embodiment, as described above, the needle 30 being in the retracted end position specifies that the distal end of the needle 30 is at the retracted end B of the path K illustrated in FIG. 3.

The hook member 28 being in the advanced position denotes that the top 280a of the hook part 280 constituting the hook member 28 is positioned at the proximal edge 34b of the depression 34 in the cylindrical member 12. The hook member 28 being at the advanced end position denotes that the tip 280b of the hook part 280 constituting the hook member 28 is positioned farther toward the distal side (advanced side) of the cylindrical member 12 than when the hook member 28 is in the advanced position. The hook member 28 being in the retracted position denotes that the tip 280b of the hook part 280 constituting the hook member 28 is positioned at the proximal end of the cylindrical member 12. The hook member 28 being in the retracted end position denotes that the top 280a of the hook part 280 constituting the hook member 28 is positioned farther toward the retracted side than the proximal end of the cylindrical member 12.

Next, a stitch forming operation and an ensuing knot forming operation for closing from the inside an opening in the biological tissue T, such as an opening in the pouch-like left atrial appendage at the site of an intra-atrial thrombus formation, will be described for the suturing device 10 having the structure described above.

<Stitch Forming Operation>

FIGS. 16 through 24 are longitudinal cross-sectional views of the suturing device 10 for describing the sequence of operations for forming a single stitch in the biological tissue T. FIGS. 25 through 32 are schematic diagrams illustrating the sequence of operations for forming a single stitch using the shuttle 26, hook member 28, and needle 30. FIG. 33 is a timing diagram describing the operations of each member that contributes to the formation of a single stitch in the biological tissue T.

Figure 16:
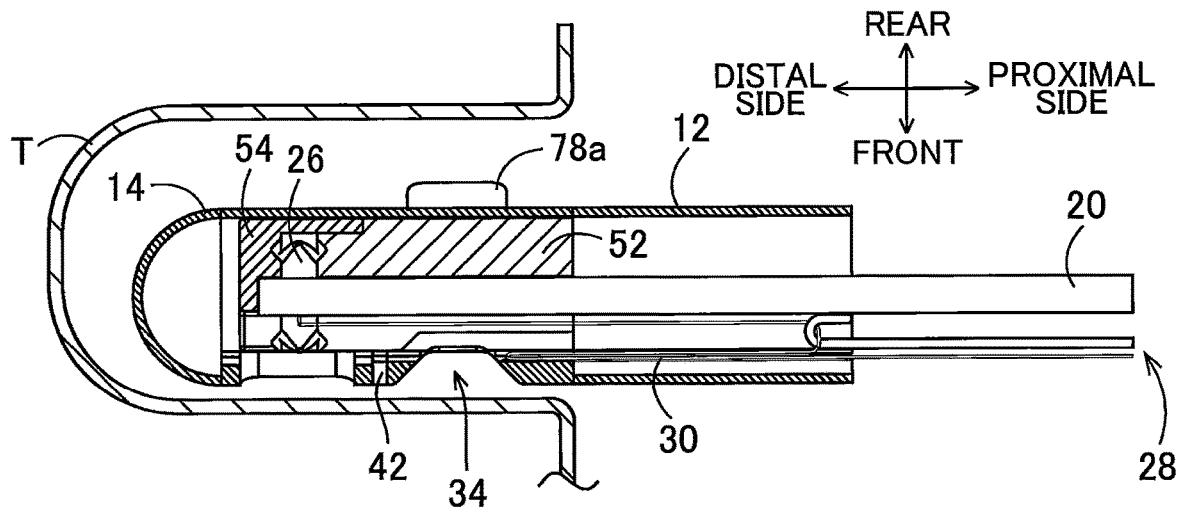
FIG. 16 is a longitudinal cross-sectional view of a distal end portion of the suturing device according to the embodiment for describing an insertion step in a single stitch forming operation with respect to a biological tissue.
Figure 25:
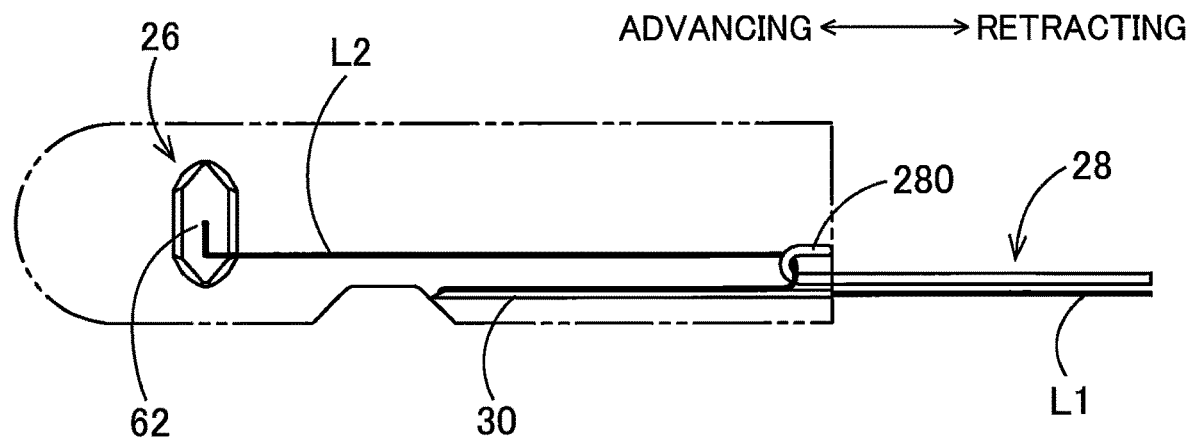
FIG. 25 is a schematic view of the distal end portion of the suturing device according to the embodiment and particularly illustrating the shuttle, a hook member, and the needle for describing the insertion step illustrated in FIG. 16 and the biological tissue fixing step illustrated in FIG. 17.

First, by operating the tubular coupling member 16 (see FIG. 1), the distal end portion of the suturing device 10 is inserted into the pouch-like biological tissue T, as indicated at timing (a) in FIG. 33. FIG. 16 is a longitudinal cross-sectional view of the suturing device 10 illustrating the initial state similar to the state illustrated in FIG. 11. FIG. 25 illustrates the insertion step for inserting the distal end of the suturing device 10 into the pouch-like biological tissue T (not illustrated). In this state, the needle 30 is in the retracted end position, and the first thread-like member L1 and second thread-like member L2 formed continuously with the first thread-like member L1 that extend between the distal end of the needle 30 and the holding part 62 of the shuttle 26 are hooked around the hook part 280 of the hook member 28 in the retracted position on the proximal side of the cylindrical member 12. At this time, the hook member 28 is in the retracted position.

Figure 17:
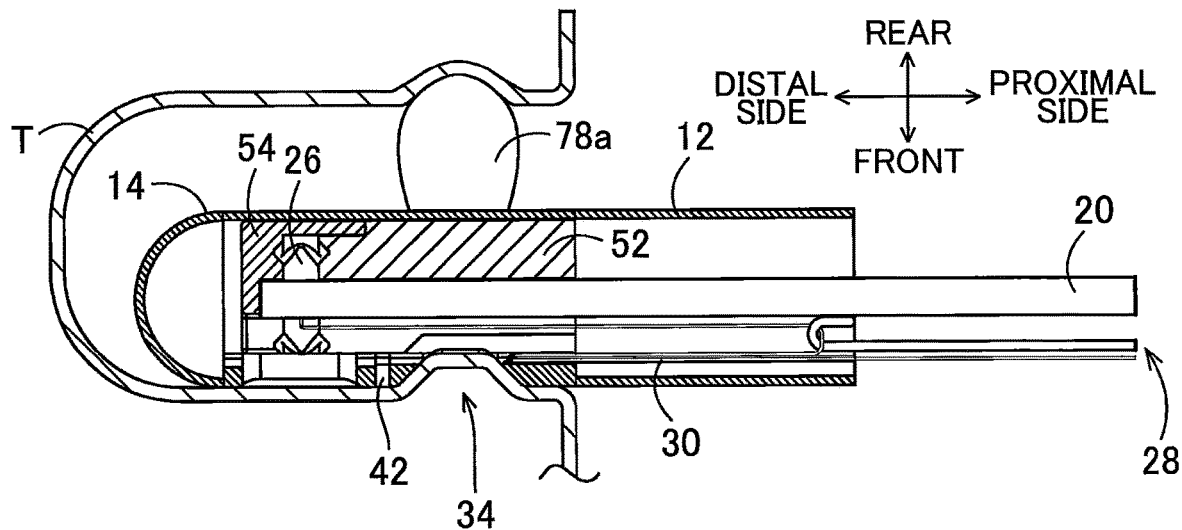
FIG. 17 is a longitudinal cross-sectional view of the distal end portion of the suturing device according to the embodiment for describing a biological tissue fixing step in the single stitch forming operation with respect to the biological tissue.

Next, a pressurized fluid is supplied through the hose (not illustrated) into the balloon 78a configuring the suturing target clamping mechanism 78 provided on the rear surface of the suturing device 10 that is inserted inside the pouch-like biological tissue T, as indicated at timing (b) in FIG. 33. As the balloon 78a expands from the pressurized fluid, tension is generated in the biological tissue T, causing a portion of the biological tissue T to be received and immobilized in the depression 34 of the suturing device 10. When a portion of the biological tissue T is immobilized in the depression 34 in this way, the path K becomes aligned with a position inside the thickness of the wall constituting the biological tissue T. FIG. 17 is a longitudinal cross-sectional view illustrating the distal end portion of the suturing device 10 in this state, and FIG. 25 illustrates this biological tissue fixing step for fixing the biological tissue T (not illustrated) with respect to the distal end portion of the suturing device 10.

Figure 18:
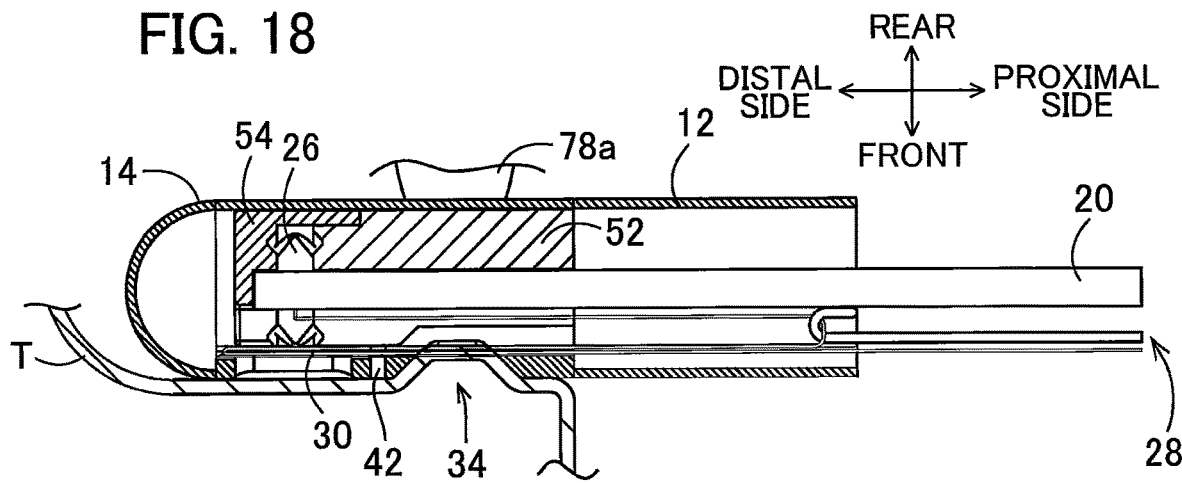
FIG. 18 is a longitudinal cross-sectional view of the distal end portion of the suturing device according to the embodiment for describing a needle piercing step in the single stitch forming operation with respect to the biological tissue.
Figure 26:
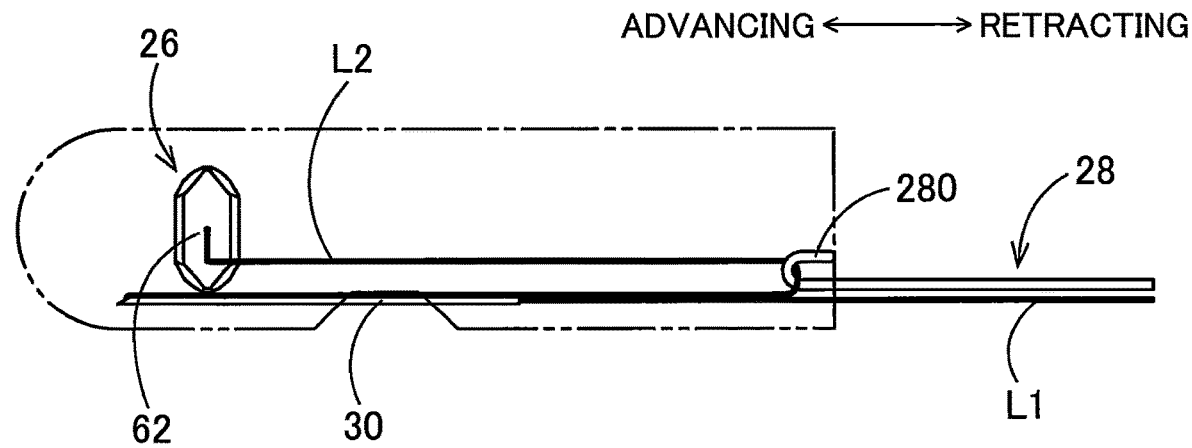
FIG. 26 is a schematic view of the distal end portion of the suturing device according to the embodiment and particularly illustrating the shuttle, the hook member, and the needle for describing the needle piercing step illustrated in FIG. 18.

Next, through an operation to advance the second operating handle 23, the needle 30 advances toward the advanced end position while the first thread-like member L1 equivalent to the advancing distance of the needle 30 is supplied into the needle 30, as indicated at timing (c) in FIG. 33. The needle 30 and the first thread-like member L1 (needle thread (upper thread)) pass through the wall of the biological tissue T positioned in the depression 34. FIG. 18 is a longitudinal cross-sectional view illustrating the distal end portion of the suturing device 10 in this state. FIG. 26 illustrates this needle piercing step for piercing the needle 30 into the wall of the biological tissue T (not illustrated) positioned in the depression 34.

Figure 19:
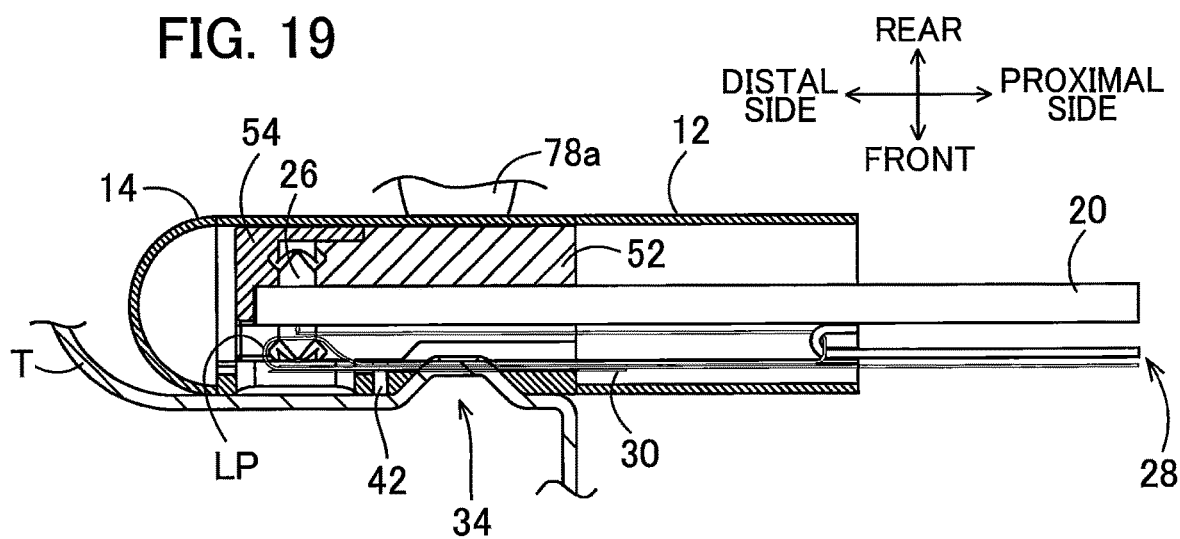
FIG. 19 is a longitudinal cross-sectional view of the distal end portion of the suturing device according to the embodiment for describing a loop forming step in the single stitch forming operation with respect to the biological tissue.
Figure 27:
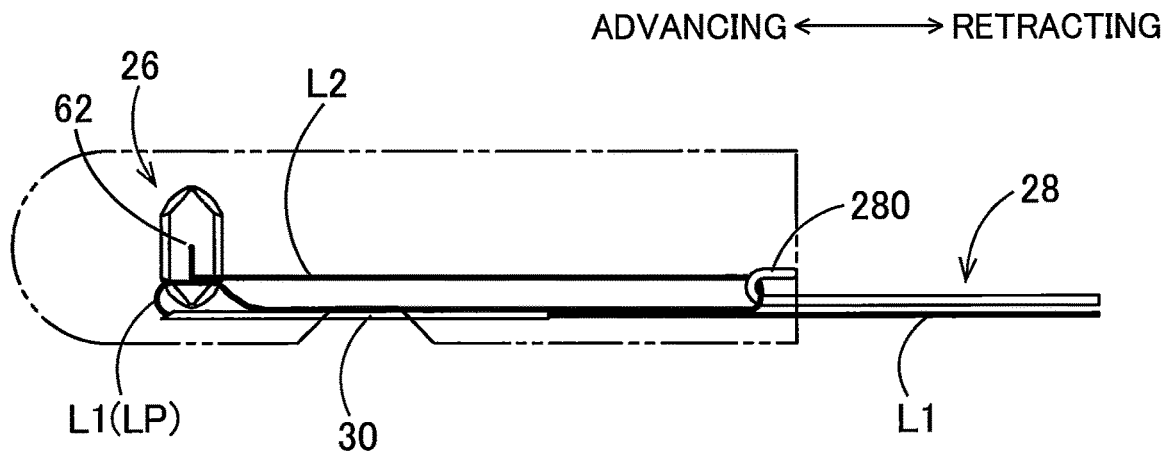
FIG. 27 is a schematic view of the distal end portion of the suturing device according to the embodiment and particularly illustrating the shuttle, the hook member, and the needle for describing the loop forming step illustrated in FIG. 19.

Through an operation to retract the second operating handle 23, the needle 30 is retracted by a small prescribed amount toward the proximal side of the cylindrical member 12, as indicated at timing (d) in FIG. 33. Through frictional resistance between the friction member 42 and the first thread-like member L1 positioned outside the distal end portion of the needle 30, a loop LP is formed at the distal end portion of the needle 30. This loop LP is formed in the loop support space within the slit 76 provided in the shuttle guide member 36 along a radial direction of the center axis C1, as illustrated in FIG. 11. FIG. 19 is a longitudinal cross-sectional view illustrating the distal end portion of the suturing device 10 in this state. FIG. 27 illustrates this loop forming step for forming a loop LP in the first thread-like member L1.

Figure 20:
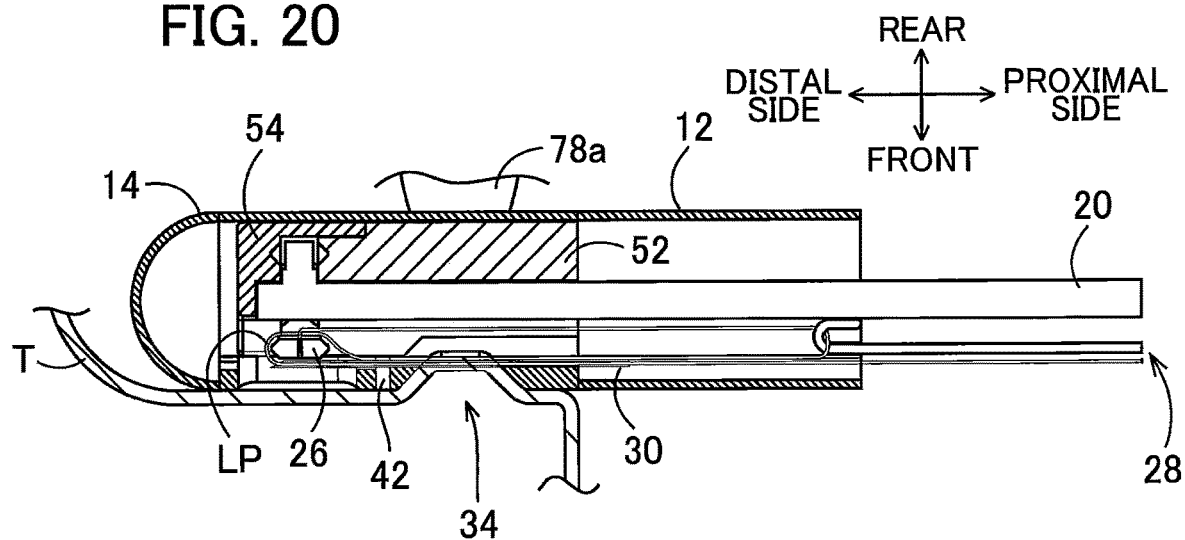
FIG. 20 is a longitudinal cross-sectional view of the distal end portion of the suturing device according to the embodiment for describing a loop threading step in the single stitch forming operation with respect to the biological tissue.
Figure 28:
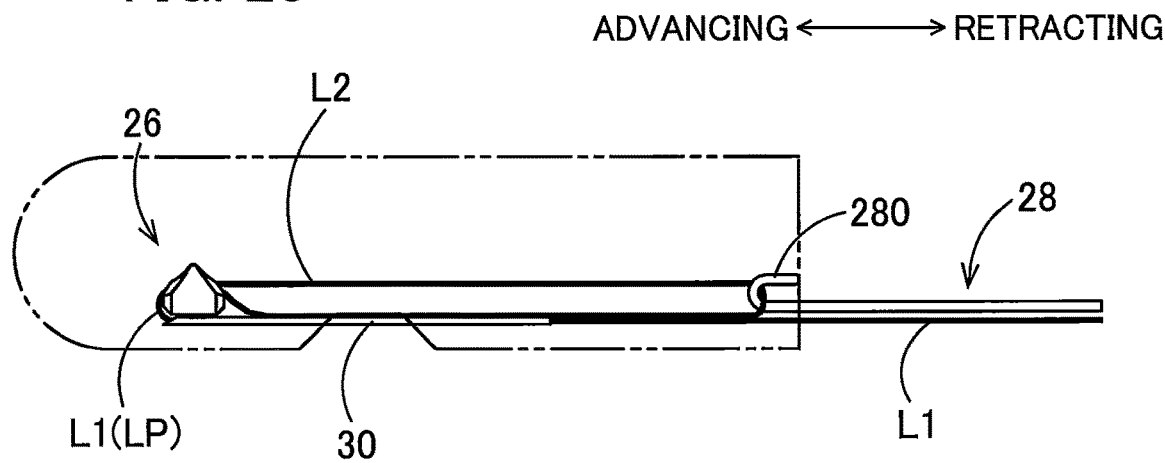
FIG. 28 is a schematic view of the distal end portion of the suturing device according to the embodiment and particularly illustrating the shuttle, the hook member, and the needle for description of the loop threading step illustrated in FIG. 20.

Next, a right-hand rotating operation is performed with the first operating handle 21 to move the pusher 58 around the center axis C1, as indicated at timing (e) in FIG. 33. At this time, the pusher 58 contacts the second hook-shaped end 66 of the shuttle 26, moving the shuttle 26 in the circumferential direction along the shuttle guide groove 56 so that the shuttle 26 passes through the loop LP, as illustrated in FIGS. 12 through 14. FIG. 20 is a longitudinal cross-sectional view illustrating a state after the first operating handle 21 has undergone a right-hand rotating operation of approximately 110 degrees and illustrating the distal end portion of the suturing device 10 when the longitudinal (circumferential) center portion of the shuttle 26 is positioned inside the loop LP. FIG. 28 illustrates a loop threading step with the shuttle 26. Through this step, the second thread-like member L2 held in the shuttle 26 is passed through the loop LP formed in the first thread-like member L1 at the distal end portion of the needle 30 so that the second thread-like member L2 intersects the loop LP of the first thread-like member L1.

Figure 21:
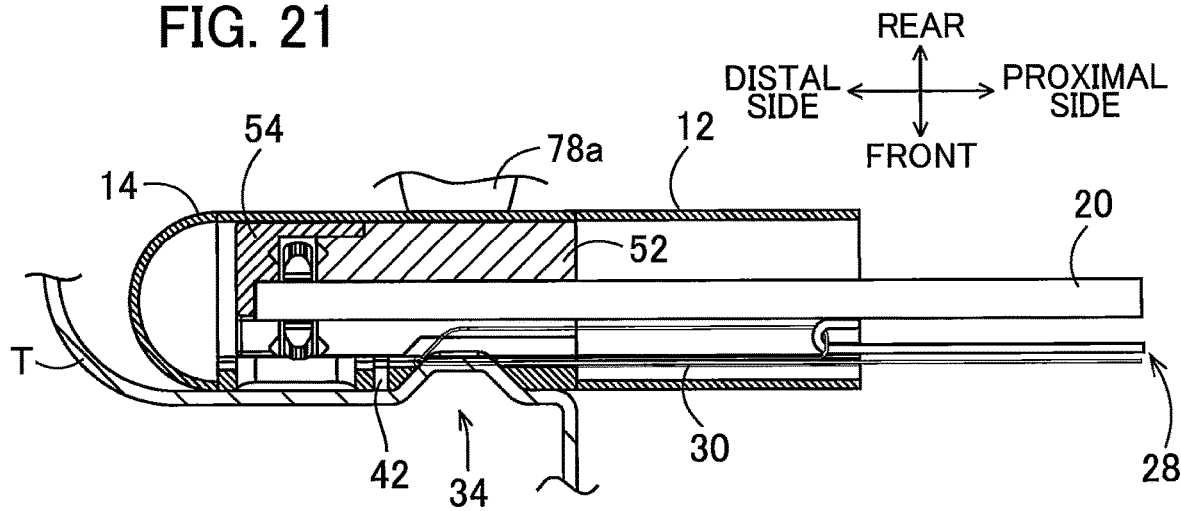
FIG. 21 is a longitudinal cross-sectional view of the distal end portion of the suturing device according to the embodiment for describing a loop tightening step in the single stitch forming operation with respect to the biological tissue.
Figure 29:
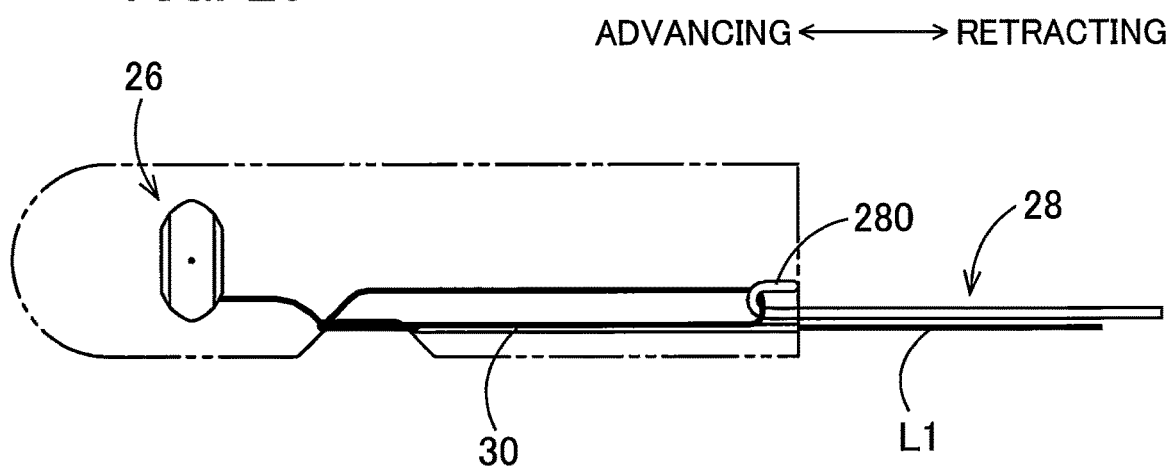
FIG. 29 is a schematic view of the distal end portion of the suturing device according to the embodiment and particularly illustrating the shuttle, the hook member, and the needle for description of the loop tightening step illustrated in FIG. 21.

Next, a retracting operation is performed on the second operating handle 23 to move the needle 30 so that the distal end of the needle 30 is retracted to a position at the retracted end B of the path K, as indicated at timing (f) in FIG. 33. Further, a left-hand rotating operation is performed with the first operating handle 21 to move the pusher 58 from the leftmost end position to the left stop position, as illustrated in FIGS. 14 and 15. Through these operations, the needle 30 is extracted from the biological tissue T, and the first thread-like member L1 (needle thread (upper thread)) is pulled and tightened, reducing the size of the loop LP. At this time, the first thread-like member L1 begins passing through the needle 30 and is supplied into the needle 30 in response to the retraction of the same so that the second thread-like member L2 is not drawn into the biological tissue T. This operation produces a stitch N with thread tension, such as those illustrated in FIGS. 34 and 35. FIG. 21 is a longitudinal cross-sectional view illustrating the distal end portion of the suturing device 10 in this state. FIG. 29 illustrates this loop tightening step for tightening the loop LP and producing a stitch N.

Figure 22:
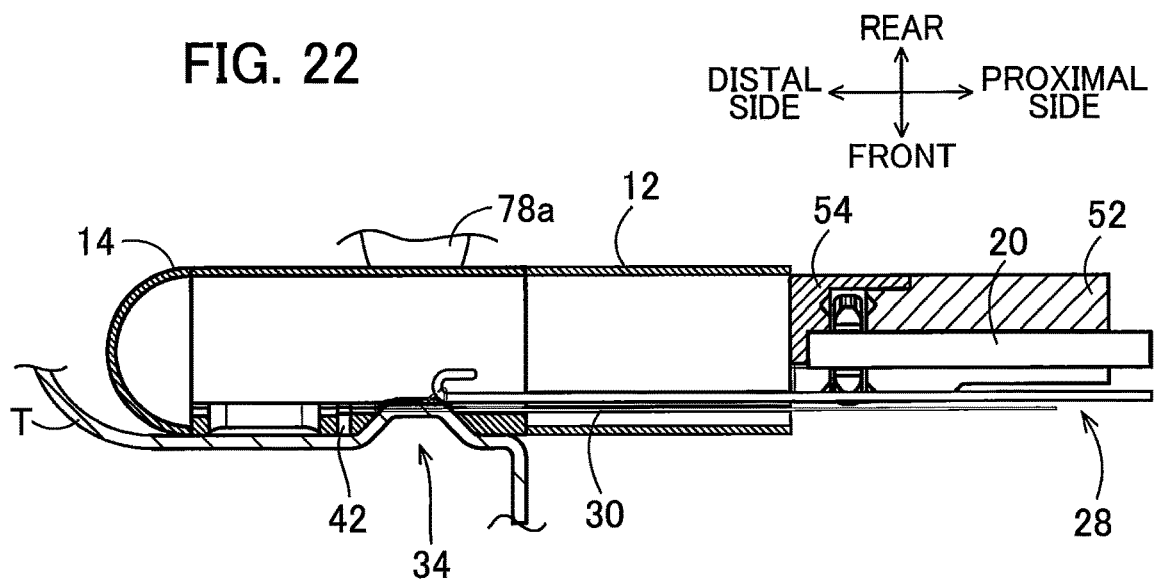
FIG. 22 is a longitudinal cross-sectional view of the distal end portion of the suturing device according to the embodiment for describing a hook advancing step in the single stitch forming operation with respect to the biological tissue.
Figure 30:
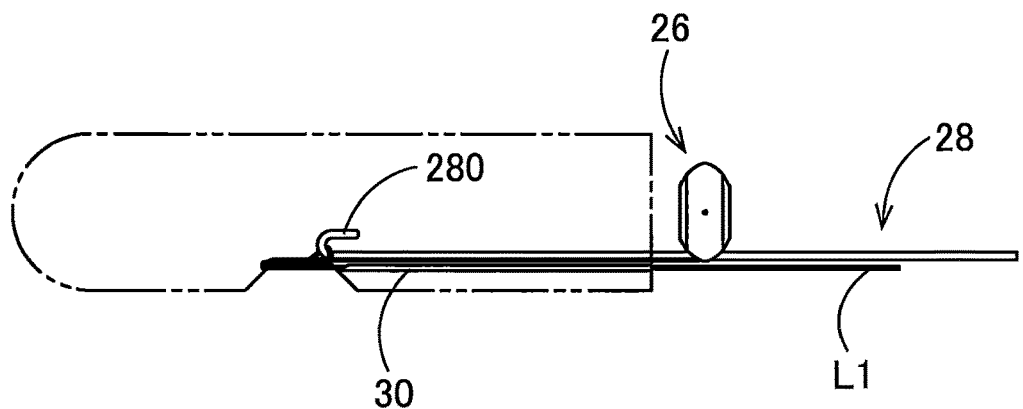
FIG. 30 is a schematic view of the distal end portion of the suturing device according to the embodiment and particularly illustrating the shuttle, the hook member, and the needle for description of the hook advancing step illustrated in FIG. 22.

A retracting operation is also performed on the first operating handle 21 to retract the shuttle guide member 36 to the proximal side of the cylindrical member 12 so that the shuttle 26 retained in the shuttle guide member 36 is retracted toward the retracted end position, as indicated at timing (g) in FIG. 33. This retracting movement of the shuttle 26 may be performed at the same time the needle 30 is retracted to the retracted end position at timing (f). In association with the retracting movement of the shuttle 26, the third operating handle 25 is operated to advance the hook member 28 until the hook part 280 reaches a position near the distal end of the needle 30 in the advanced end position. FIG. 22 is a longitudinal cross-sectional view illustrating the distal end portion of the suturing device 10 in this state. FIG. 30 illustrates this hook advancing step for advancing the hook member 28. When the shuttle 26 is retracted to the retracted position, the hook member 28 is advanced toward the distal end of the cylindrical member 12. At this time, the first operating shaft 20 moves in the direction from the proximal end toward the distal end of the cylindrical member 12 a distance corresponding to half the distance that the shuttle 26 is retracted to the retracted end position.

Figure 23:
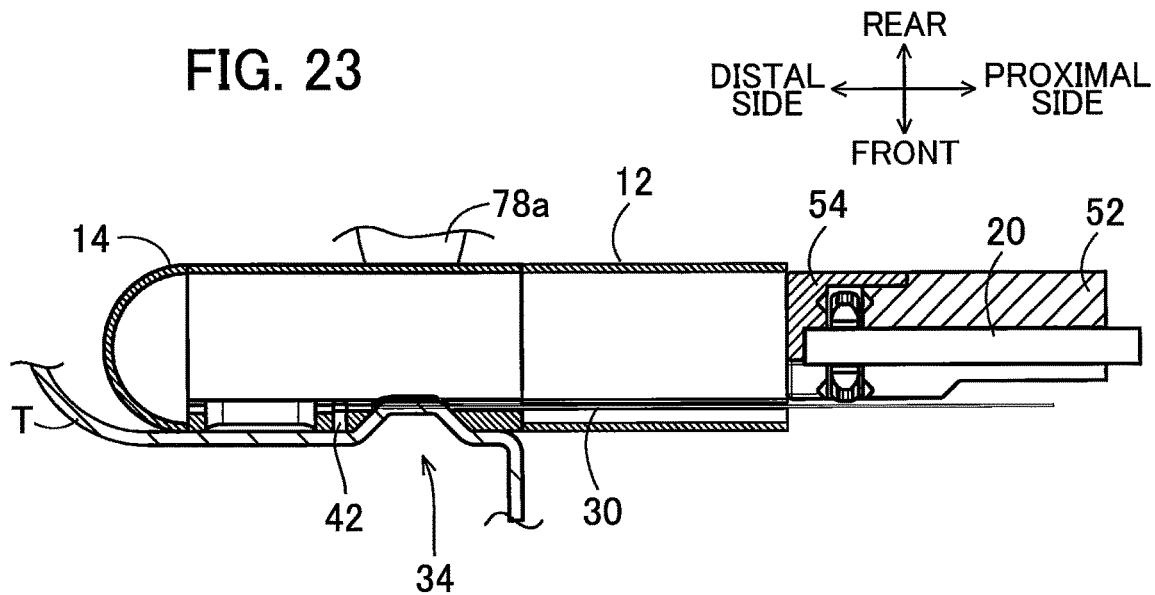
FIG. 23 is a longitudinal cross-sectional view of the distal end portion of the suturing device according to the embodiment for describing a hook-thread detaching step in the single stitch forming operation with respect to the biological tissue.
Figure 31:
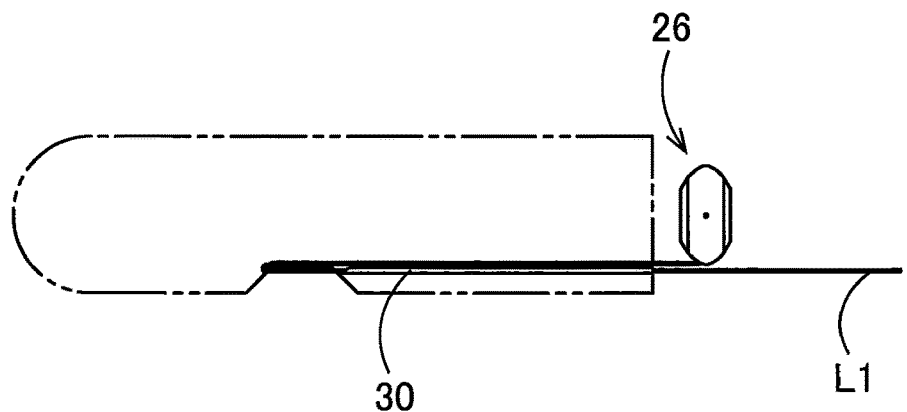
FIG. 31 is a schematic view of the distal end portion of the suturing device according to the embodiment and particularly illustrating the shuttle and the needle for description of the hook-thread detaching step illustrated in FIG. 23.

Next, an advancing operation and a half-turn operation are performed on the third operating handle 25, as indicated at timing (h) in FIG. 33, whereby the hook member 28 is moved farther toward the distal side of the cylindrical member 12 until the hook part 280 is separated from the loop LP, and is subsequently rotated a half turn to detach the hook part 280 from the loop LP. Further, a retracting operation is performed on the third operating handle 25, at timing (h) in FIG. 33 (not indicated), to move the hook member 28 from the advanced end position to a position farther toward the retracted side than the retracted end position. FIG. 23 is a longitudinal cross-sectional view illustrating the distal end portion of the suturing device 10 in this state. FIG. 31 illustrates this hook-thread detaching step for detaching the hook part 280 from the loop LP. FIGS. 23 and 31 illustrate the state after the hook member 28 has been turned in a right-hand rotation at its advanced end position to be detached from the loop LP and subsequently retracted farther toward the retracted side than the proximal end of the cylindrical member 12. Consequently, the hook member 28 is not illustrated in FIGS. 23 and 32. Subsequently, an advancing operation is performed on the third operating handle 25 to move the hook member 28 back to the advanced end position. At this time, the hook member 28 is detached from the loop LP at its advanced end position. This movement of the hook member 28 is also not indicated but is performed at the timing (h) in FIG. 33.

Figure 24:
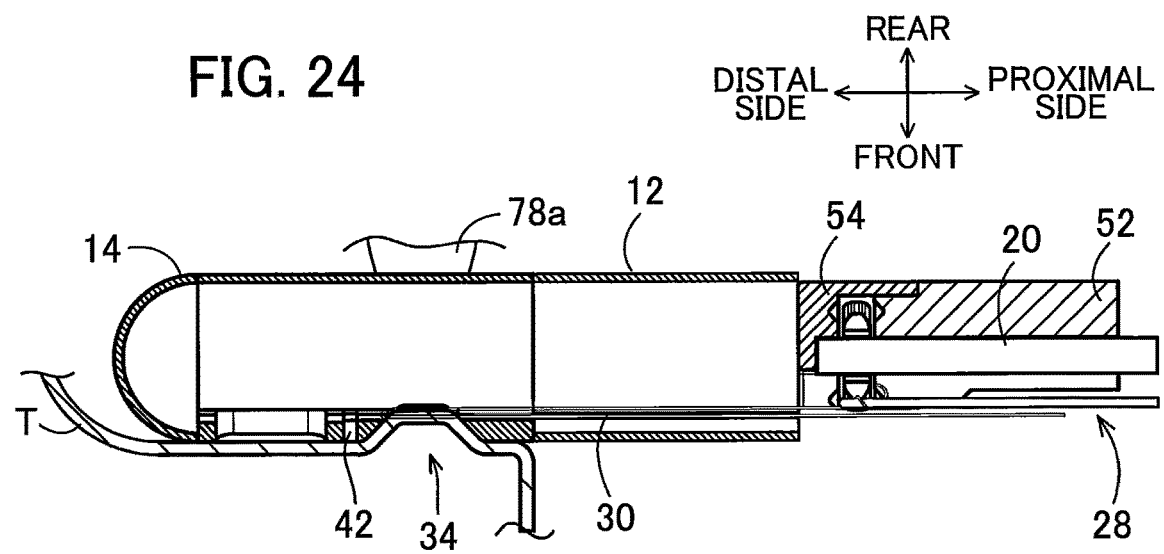
FIG. 24 is a longitudinal cross-sectional view of the distal end portion of the suturing device according to the embodiment for describing a thread hooking step in the single stitch forming operation with respect to the biological tissue.
Figure 32:
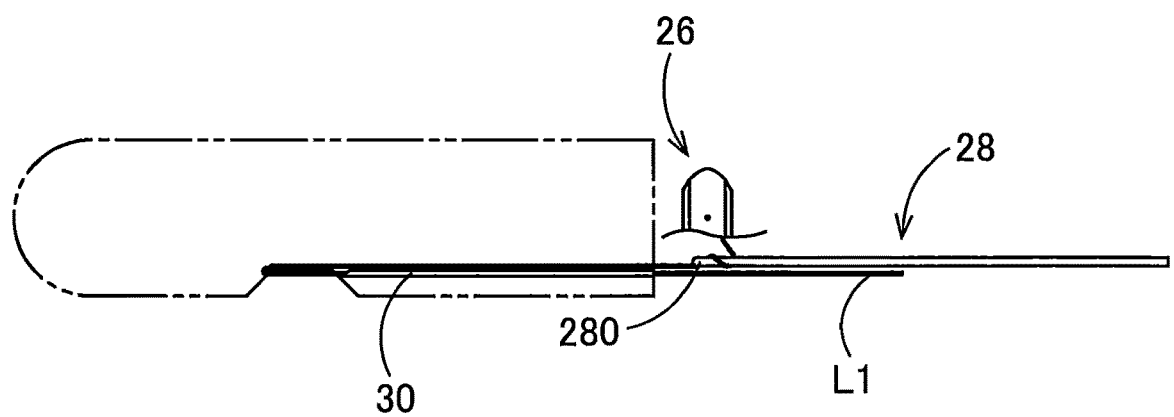
FIG. 32 is a schematic view of the distal end portion of the suturing device according to the embodiment and particularly illustrating the shuttle, the hook member, and the needle for description of the thread hooking step illustrated in FIG. 24.

Next, a retracting operation is performed on the third operating handle 25, as indicated at timing (i) in FIG. 33, whereby the hook member 28 is retracted to the retracted end position near the position of the shuttle 26 in the retracted end position. When the hook member 28 is in the retracted end position, the hook part 280 is detached from the first thread-like member L1. Subsequently, a left-hand rotating operation is performed with the third operating handle 25. At this time, the hook member 28 is also moved slightly toward the distal side of the cylindrical member 12 so that the hook part 280 is positioned on the distal side of the cylindrical member 12 (on the advanced side) relative to the shuttle 26 while the hook member 28 is rotated one turn. The hook part 280 of the hook member 28 hooks the second thread-like member L2 positioned between the reduced loop LP and the shuttle 26. FIG. 24 is a longitudinal cross-sectional view illustrating the distal end portion of the suturing device 10 in this state. FIG. 32 illustrates this thread hooking step for hooking the second thread-like member L2 by the hook part 280 of the hook member 28.

Figure 34:
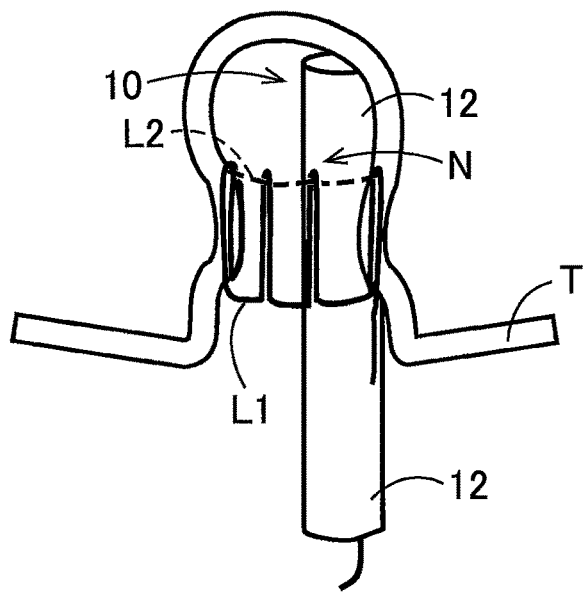
FIG. 34 is a schematic perspective view illustrating a state where a plurality of stitches is formed annularly in succession along an inner circumferential surface of a pouch-like biological tissue, using the suturing device according to the embodiment.

Subsequently, the balloon 78a configuring the suturing target clamping mechanism 78 provided on the rear surface of the suturing device 10 is shrunk, as indicated at timing (j) in FIG. 33, by discharging the pressurized fluid from the balloon 78a through the hose (not illustrated). At the same time, an advancing operation is performed with the first operating handle 21 to advance the shuttle guide member 36 accommodating the shuttle 26 to the position illustrated in FIG. 20, i.e., the advanced end position, and an advancing operation and rotating operation are performed with the third operating handle 25 to advance the hook member 28 to the position illustrated in FIG. 17 and to return the hook member 28 half turn. These operations restore the components to their positions in the initial state illustrated in FIG. 17 for the start of a stitch. Thereafter, a plurality of stitches N are formed in sequence by repeatedly rotating the suturing device 10 within the pouch-like biological tissue T to the next stitch forming position and performing the same stitch forming operations described above. FIG. 34 is a schematic diagram illustrating this operation.

Figure 35:
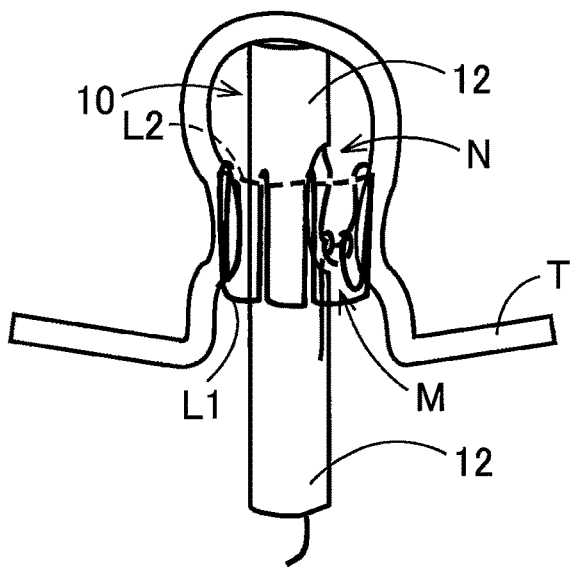
FIG. 35 is a schematic perspective view illustrating a state where a knot is formed to prevent the stitches from unravelling after the plurality of stitches is formed over an entire circumference of the inner surface of the pouch-like biological tissue, using the suturing device according to the embodiment.
Figure 36:
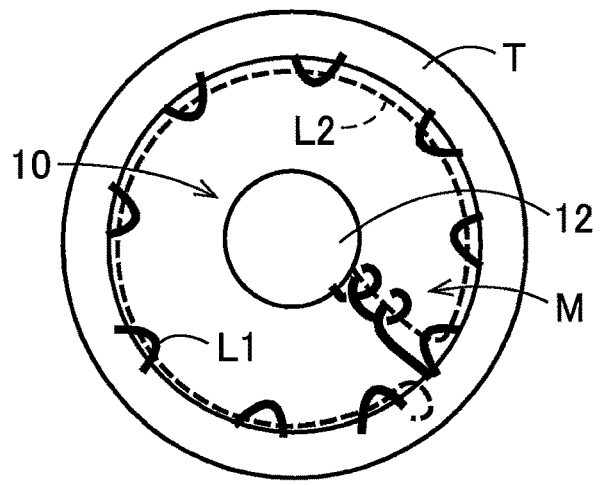
FIG. 36 is a schematic view illustrating a cross-section of the structures illustrated in FIG. 35.
Figure 37:
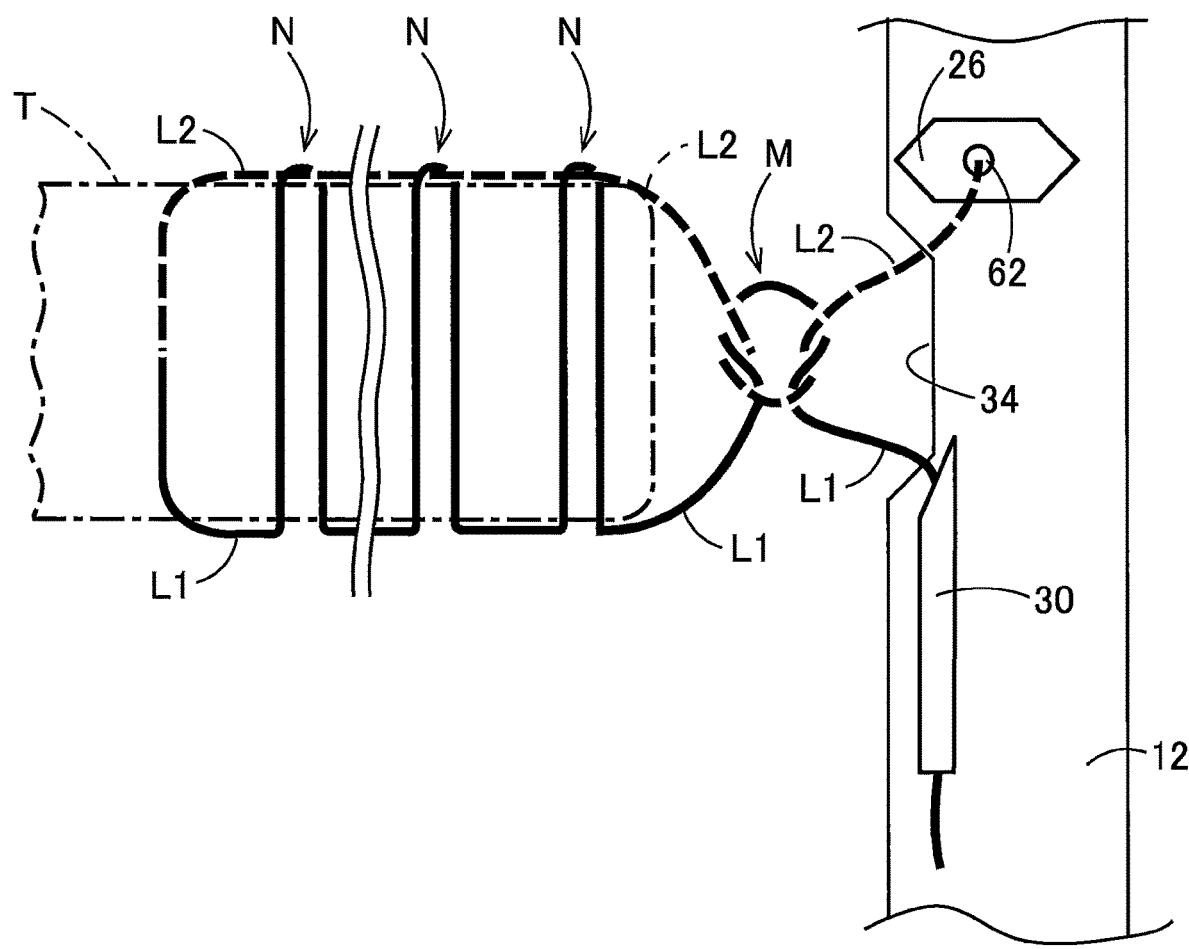
FIG. 37 is a developed view illustrating a state where the plurality of stitches is formed annularly in succession along the inner circumferential surface of the pouch-like biological tissue and the knot is formed following the stitches with the first thread-like member and a second thread-like member, using the suturing device according to the embodiment.

After stitches N have been formed across substantially the entire inner circumferential surface of the biological tissue T, as described above, a knot M is formed with the suturing device 10 using the first thread-like member L1 and second thread-like member L2, as illustrated in the sample schematic diagram of FIG. 35, so that the stitches N cannot unravel. FIG. 36 is a cross-sectional view of the structures illustrated in FIG. 35. FIG. 37 is a developed view illustrating a plurality of stitches N formed annularly in succession along the inner circumferential surface of the biological tissue T protruding in a pouch-like formation, and a knot M formed following the stitches N with the first thread-like member L1 and second thread-like member L2. As illustrated in FIG. 37, the first thread-like member L1 and second thread-like member L2 are different portions of the same thread-like member L. The first thread-like member L1 constitutes the section of the thread-like member L held by the needle 30 and drawn out from the distal end portion of the needle 30 to the biological tissue T, and the second thread-like member L2 constitutes the section of the thread-like member L held in the shuttle 26 and drawn out from the shuttle 26 to the biological tissue T.

<Knot Forming Operation>

Figure 42:
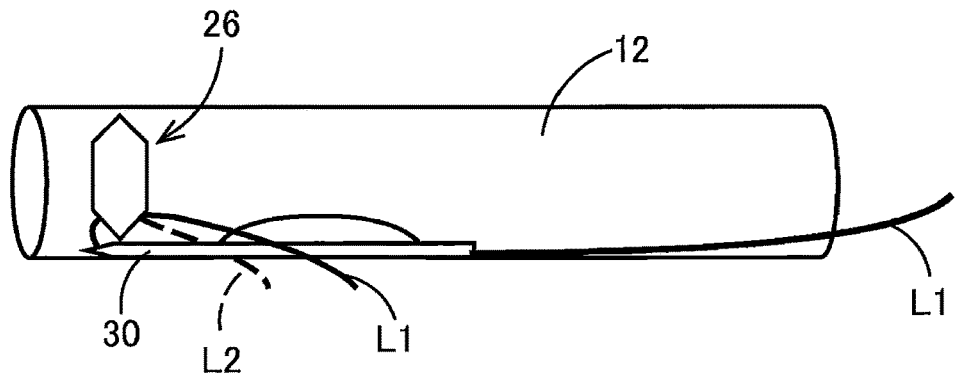
FIG. 42 is a schematic view of the cylindrical member of the suturing device according to the embodiment and particularly illustrating the shuttle and the needle for describing a loop threading step in the half hitch forming operation.
Figure 43:
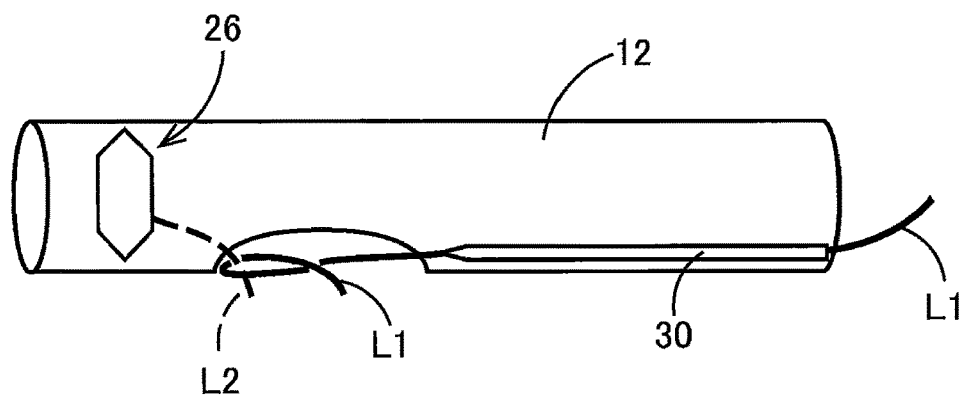
FIG. 43 is a schematic view of the cylindrical member of the suturing device according to the embodiment and particularly illustrating the shuttle and the needle for describing a needle retracting step in the half hitch forming operation.
Figure 44:
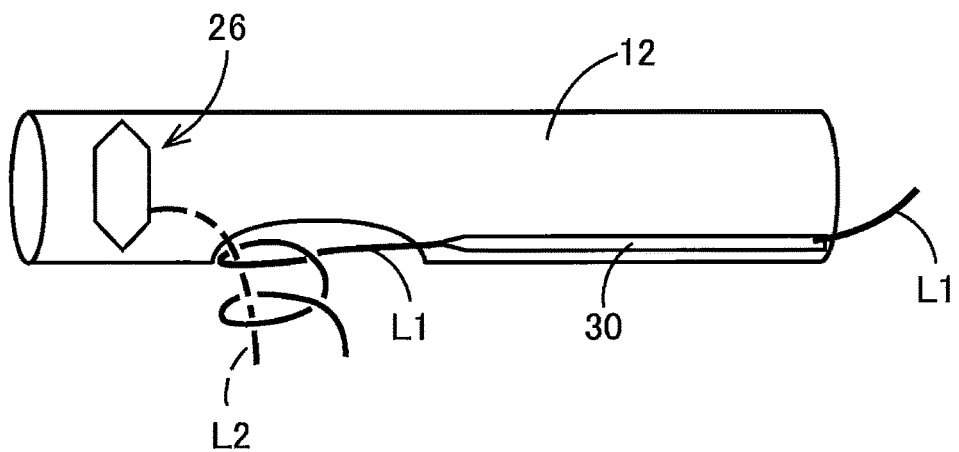
FIG. 44 is a schematic view illustrating a primitive form of a knot obtained by performing a half hitch forming operation at a first stage operation and a half hitch forming operation at a second stage operation the same as the first stage operation in accordance with the half hitch forming operation attendant to FIGS. 38 through 43.
Figure 45:
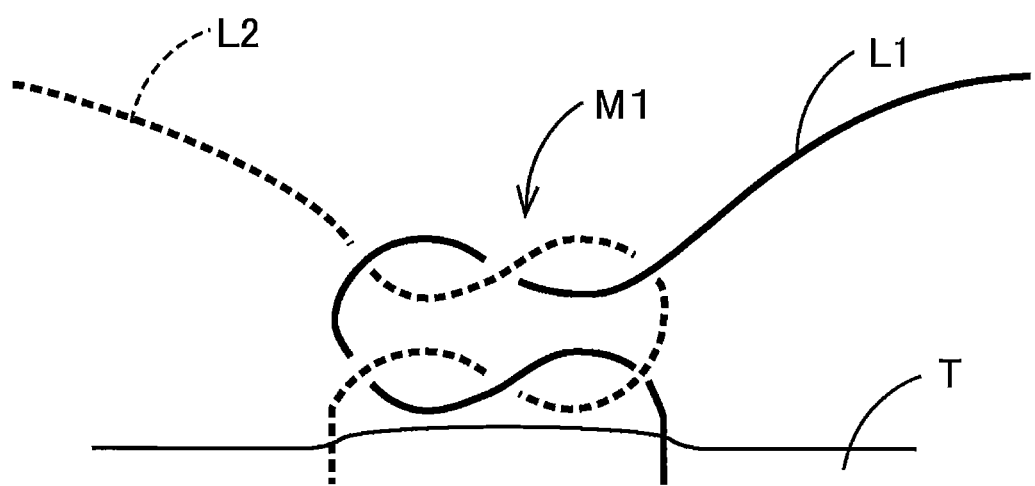
FIG. 45 illustrates a granny knot produced by reshaping the primitive from of the knot illustrated in FIG. 44.

FIGS. 38 through 43 are schematic diagrams illustrating a sequence of operations performed with the suturing device 10 to form a half hitch using the first thread-like member L1 and second thread-like member L2. FIG. 44 is a schematic diagram illustrating the primitive form of a knot M1 obtained by performing this half hitch forming operation twice. FIG. 45 illustrates the granny knot M1 produced by reshaping the primitive form in FIG. 44.

FIGS. 46 and 47 are timing diagrams illustrating the operations of members that contribute to formation of a single half hitch. The timing diagram in FIG. 47 illustrates an operation pattern A in which the needle 30 has a right-hand rotation for winding the first thread-like member L1 (denoted NEEDLE CWR in FIG. 50 described later) and the shuttle 26 passes through the loop LP while moving in a right-hand circumferential direction (denoted SHUTTLE CWR in FIG. 50 described later). The timing diagram in FIG. 47 illustrates an operation pattern B in which the needle 30 has a left-hand rotation for winding the first portion L1 of the thread-like member L (denoted NEEDLE CCR in FIG. 50 described later) and the shuttle 26 passes through the loop LP while moving in a left-hand circumferential direction (denoted SHUTTLE CCR in FIG. 50 described later). The balloon 78a configuring the suturing target clamping mechanism 78 is not used in the knot forming operations since the needle 30 is not inserted into the biological tissue T. Further, the hook member 28 has been omitted from FIGS. 38 through 44.

Figure 38:
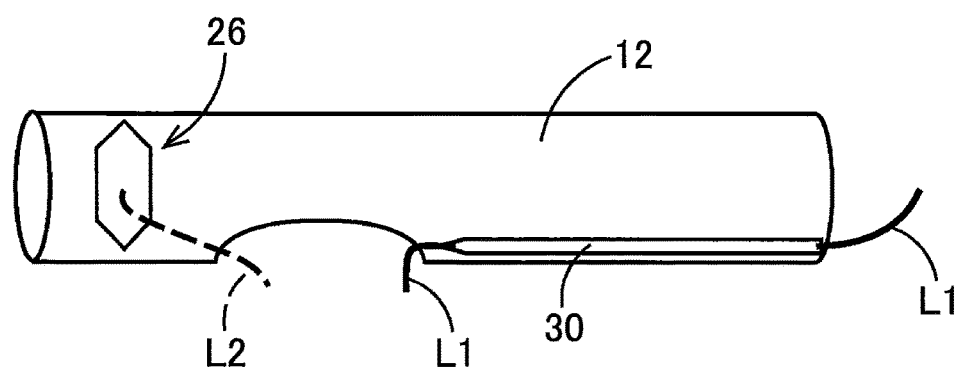
FIG. 38 is a schematic view of the cylindrical member of the suturing device according to the embodiment and particularly illustrating the shuttle and the needle for describing an insertion step in a half hitch forming operation.

First, while the distal end portion of the suturing device 10 remains inserted in the pouch-like biological tissue T, the balloon 78a constituting the suturing target clamping mechanism 78 disposed on the rear surface of the suturing device 10 is reduced in size to remove the biological tissue T from the depression 34, as indicated at timing (k) in FIG. 46. FIG. 38 illustrates this initial step for forming a knot. In the initial state of this knot forming operation, the needle 30 is in the retracted end position and the hook member 28 is in the proximal side of the cylindrical member 12, specifically, in the retracted position.

Figure 39:
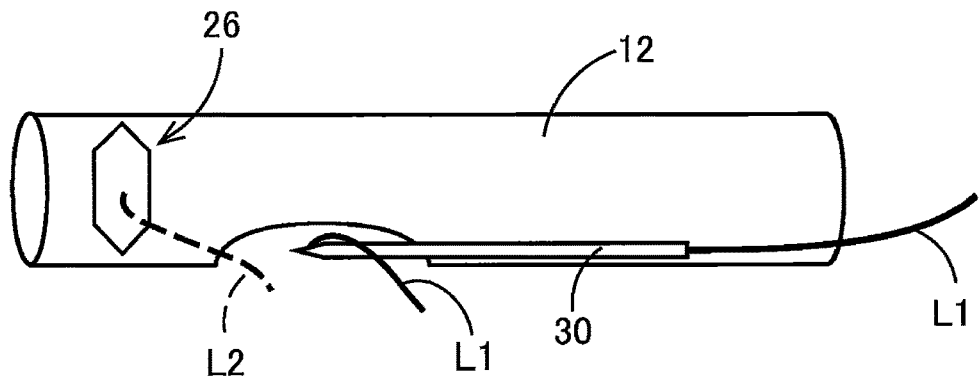
FIG. 39 is a schematic view of the cylindrical member of the suturing device according to the embodiment and particularly illustrating the shuttle and the needle for describing a thread winding step in the half hitch forming operation.

Next, an advancing operation performed with the second operating handle 23 advances the needle 30 a prescribed distance into the depression 34, while a rotating operation performed with the second operating handle 23 rotates the needle 30 one right-hand turn during the needle 30 being positioned in the depression 34, as indicated at timing (l) in FIG. 46. The rotation of the needle 30 causes the first portion L1 of the thread-like member L to wrap around the needle 30. Note that the needle 30 need not be rotated exactly one turn, but should be rotated approximately between 0.5 and 1.5 turns, for example. FIG. 39 illustrates this thread winding step for winding the thread around the needle 30.

Figure 40:
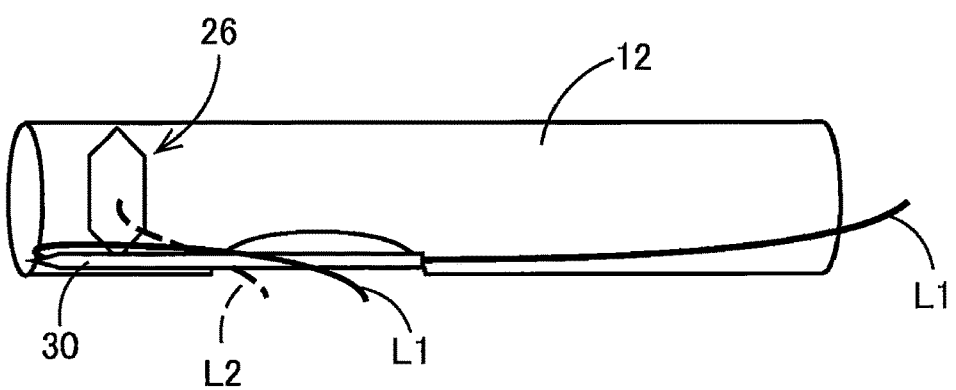
FIG. 40 is a schematic view of the cylindrical member of the suturing device according to the embodiment and particularly illustrating the shuttle and the needle for describing a needle advancing step in the half hitch forming operation.

Next, an advancing operation performed on the second operating handle 23 advances the needle 30 farther toward the distal side of the cylindrical member 12 to the advanced end position corresponding to the advanced end A of the path K, as indicated a timing (m) in FIG. 46. FIG. 40 illustrates this needle advancing step for advancing the needle 30 to the advanced end position.

Figure 41:
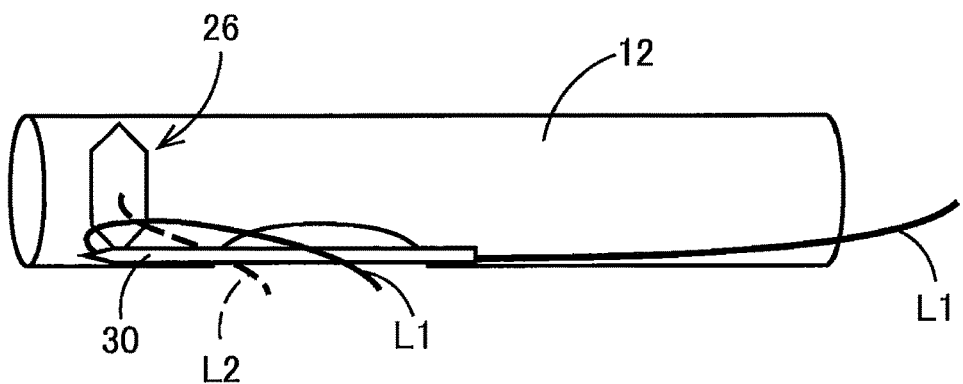
FIG. 41 is a schematic view of the cylindrical member of the suturing device according to the embodiment and particularly illustrating the shuttle and the needle for describing a loop forming step in the half hitch forming operation.

Further, a retracting operation is performed with the second operating handle 23 to retract the needle 30 a small prescribed distance toward the proximal side of the cylindrical member 12, as indicated at timing (n) in FIG. 46. Through this operation, the first thread-like member L1 positioned outside the distal end portion of the needle 30 forms a loop LP on the distal end portion of the needle 30 owing to the frictional resistance from the friction member 42. This loop LP is formed between one end (hereinafter called first end) and another end (hereinafter called second end) of the first thread-like member L1 so that a first intersecting point P1 and a second intersecting point P2 of the first thread-like member L1 intersect each other. Here, the first intersecting point P1 and second intersecting point P2 are positioned in order from the second end toward the first end. The loop LP is formed in the loop support space in the slit 76 provided in the shuttle guide member 36 in the radial direction toward the center axis C1 thereof. FIG. 41 illustrates this loop forming step for forming the loop LP in the first thread-like member L1.

Next, a right-hand rotating operation performed on the first operating handle 21 pivotally moves the pusher 58 about the center axis C1, as indicated at timing (o) of FIG. 46. At this time, the pusher 58 contacts the second hook-shaped end 66 of the shuttle 26, moving the shuttle 26 in a circumferential direction along the shuttle guide groove 56 so that the shuttle 26 passes through the loop LP. FIG. 42 illustrates this loop threading step. In this step, the end of the second thread-like member L2 held in the shuttle 26 is passed through the loop LP formed at the distal end portion of the needle 30 by the first thread-like member L1 intersecting itself at the first intersecting point P1 and second intersecting point P2 in the direction from the second intersecting point P2 toward the first intersecting point P1 of the loop LP. Accordingly, the second thread-like member L2 passes relative to the loop LP of the first thread-like member L1.

Next, a retracting operation is performed on the second operating handle 23 to retract the needle 30 until the distal end of the needle 30 is positioned at the retracted end B of the path K, as indicated at timing (p) in FIG. 46. Through this action, a half hitch is formed with the second thread-like member L2 passing through the loop LP formed in the first thread-like member L1 (needle thread (upper thread)). FIG. 43 illustrates this needle retracting step for forming a half hitch.

The operations specified at timings (q), (r), (s), and (t) in FIG. 46 are performed to return the shuttle 26 and hook member 28 to their initial positions and are identical to the operations at timings (g), (h), (i), and (j) in FIG. 33 except that the balloon 78a configuring the suturing target clamping mechanism 78 remains reduced in size. Note that the operations at timings (q), (r), (s), and (t) in FIG. 47 described later are also identical to those at timings (g), (h), (i), and (j) in FIG. 33 except that the balloon 78a configuring the suturing target clamping mechanism 78 remains reduced in size.

Thereafter, the operations for forming a half hitch illustrated in FIGS. 38 through 43 are repeated to form the primitive form of a granny knot M1, as illustrated in FIG. 44. FIG. 45 illustrates the granny knot M1 that is reshaped from the primitive form described above by tightening the first thread-like member L1 and second thread-like member L2. In other words, the granny knot M1 is formed by forming half hitches in two stages using the same operation pattern. After the granny knot M1 has been formed in this way, the suturing device 10 is extracted from the biological tissue T to tighten the first thread-like member L1 and second thread-like member L2 and, when necessary, the same operations described above may be repeated to form an additional granny knot M1 or the like. Subsequently, the process is completed by cutting off the ends of the first thread-like member L1 and second thread-like member L2.

FIG. 47 differs from FIG. 46 in that the needle 30 is rotated one left-hand turn while positioned in the depression 34 through a rotating operation on the second operating handle 23 at timing (l) to wind the first thread-like member L1 about the needle 30, and in that the shuttle 26 is passed through the loop LP in the left-hand circumferential direction through a left-hand rotating operation on the first operating handle 21 when passing through the shuttle 26 through the loop LP at timing (o). All other operations in FIG. 47 are identical to those in FIG. 46. By performing the half hitch forming operations twice according to an operation pattern B illustrated in FIG. 47, the granny knot M1 illustrated in FIG. 45 can be obtained.

However, the knot M may be formed by first executing the half hitch forming operations according to an operation pattern A illustrated in FIG. 46 and subsequently executing the half hitch forming operations according to the operation pattern B illustrated in FIG. 47. In this case, the primitive form of a square knot M2 will be formed, as illustrated in FIG. 48. FIG. 49 illustrates the square knot M2 that is reshaped from the primitive form described above by tightening the first thread-like member L1 and second thread-like member L2. This square knot M2 may also be formed by first executing the half hitch forming operations according to the operation pattern B illustrated in FIG. 47 and subsequently executing the half hitch operations according to the operation pattern A illustrated in FIG. 46. Hence, the square knot M2 is formed by forming half hitches in two stages according to different operation patterns. FIG. 50 is a table illustrating the relationships between first-stage operation patterns and second-stage operation patterns and the types of knots they produce.

Figure 51:
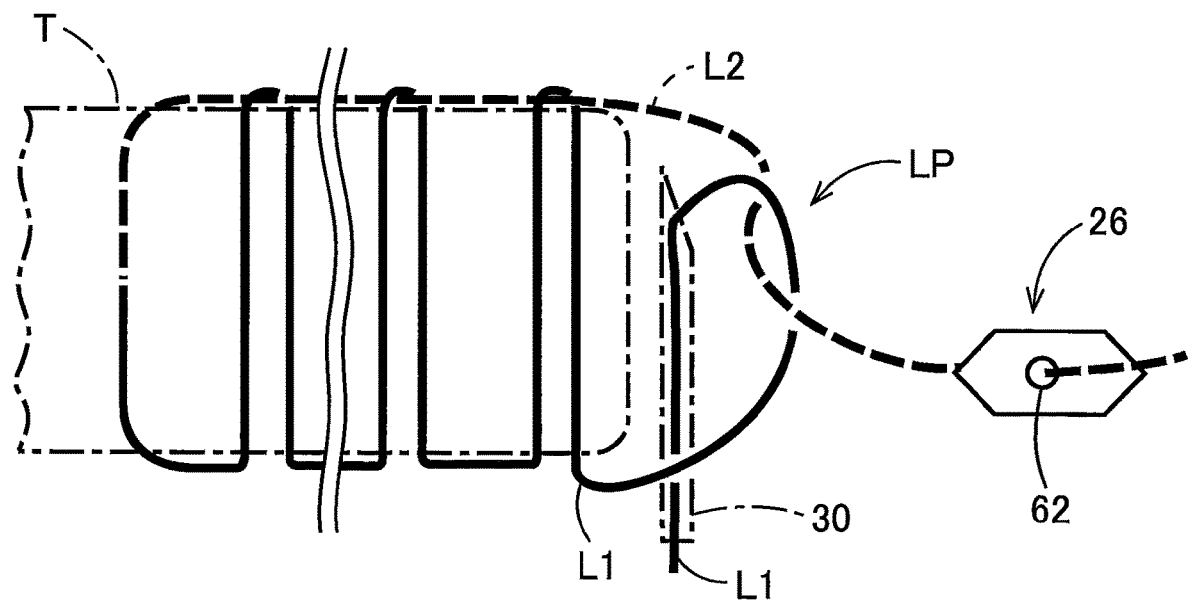
FIG. 51 illustrates a state where the second thread-like member held in a holding part of the shuttle has been passed through the loop formed in the first thread-like member in the operation illustrated in FIGS. 38 and 39.

FIG. 51 illustrates the state in which the second thread-like member L2 held in the holding part 62 of the shuttle 26 has been passed through the loop LP formed in the first thread-like member L1 at the distal end portion of the needle 30 through the operations from FIGS. 38 through 42. This loop LP may maintain an equivalent topology with a closed path. Here, the second thread-like member L2 constituting one end portion of the thread-like member L formed continuously with the first thread-like member L1 constituting another end portion of the thread-like member L must be passed through the loop LP formed in the first thread-like member L1 in order to form a half hitch as a fundamental operation for forming a secure knot M. However, among the two directions in which the second thread-like member L2 can be passed through the loop LP, one direction forms a knot and the other does not. A knot is not formed when the second thread-like member L2 is passed in the other direction because the loop LP disappears before the second thread-like member L2 can pass therethrough and is no longer a loop at the moment of passing. This concept will be described in greater detail with reference to FIG. 52.

Figure 52:
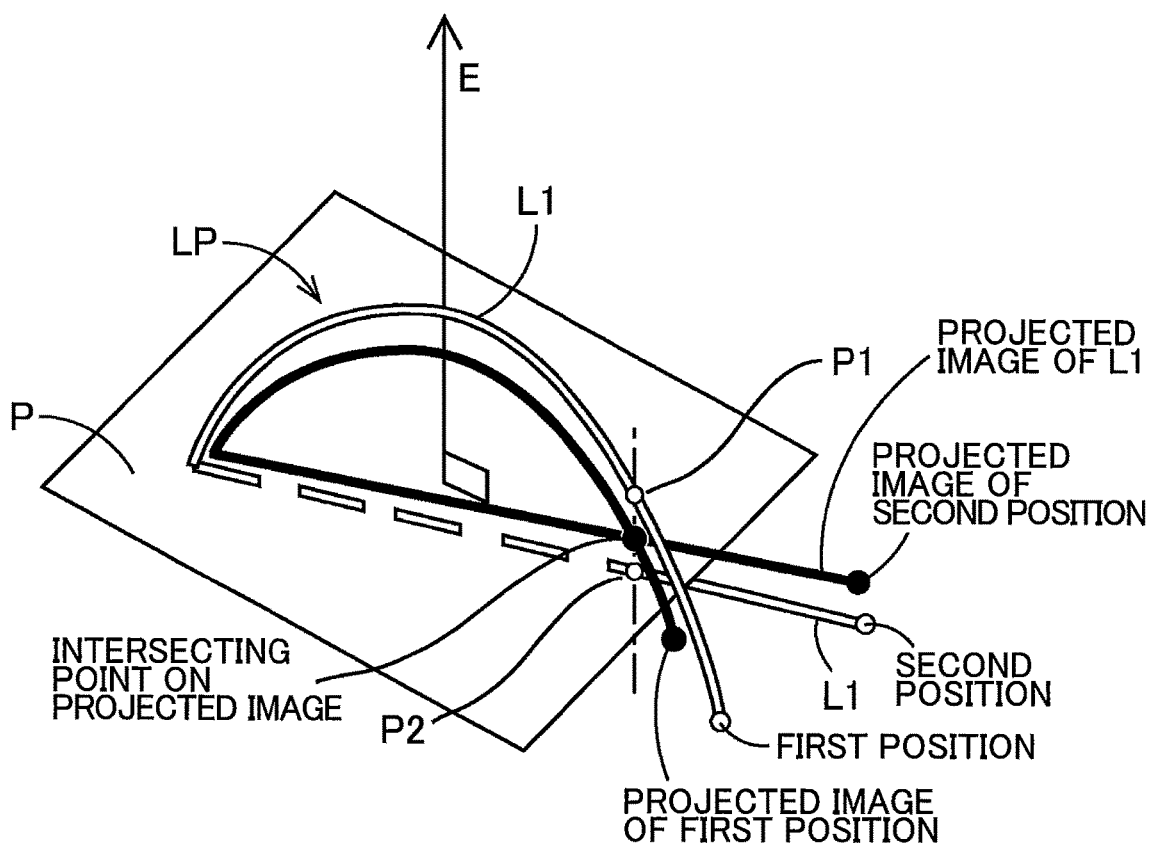
FIG. 52 is a schematic diagram illustrating that a loop defined by a virtual axis and the first thread-like member in which the loop is formed are projected onto a projecting plane orthogonal to the virtual axis.

In FIG. 52 a loop LP defined by a virtual axis E and the first thread-like member L1 in which the loop LP is formed are projected onto a projecting plane P orthogonal to the virtual axis E. When the projected image of the first thread-like member L (black lines) forms a closed path, the parts of the actual first thread-like member L1 (white lines) projected on the intersecting point of this closed path is a multilevel intersection configured of two points on the first thread-like member L, and specifically a first intersecting point P1 that is closer to a first position, which is a first end of the thread-like member L (the fixed end, and specifically the end on the biological tissue T side in the present embodiment), and a second intersecting point P2 that is farther from the first position (a position inside the needle 30). The portion of the first thread-like member L1 depicted with a dashed white line in FIG. 52 indicates the portion positioned below the projecting plane P. In this state, a knot can be formed by passing the second thread-like member L2 held in the holding part 62 of the shuttle 26 through the loop LP in a direction from the side of the second intersecting point P2 farther from the first position toward the side of the first intersecting point P1 closer to the first position, i.e., in the direction of the arrow indicating the virtual axis E.

This relationship is always satisfied regardless how the virtual axis E is established. In other words, when the loop LP is formed by the intersection of the first intersecting point P1 nearer to the first position on the side of the biological tissue T, which is the suturing target of the first thread-like member L1, and the second intersecting point P2 farther than the first intersecting point P1 from the first position through the operations in FIGS. 38 through 42, a half hitch is formed by passing the holding part 62 of the shuttle 26 holding the second thread-like member L2 through the loop LP in a direction from the side of the second intersecting point P2 toward the side of the first intersecting point P1.

Using the example of FIG. 52, if the second intersecting point P2 is a first point on the first thread-like member L1 and the first intersecting point P1 is a second point on the first thread-like member L1 that is farther than the first point from the needle 30, a knot is formed by passing the holding part 62 holding the second thread-like member L2 through the loop LP formed by the intersection of the first point on the first thread-like member L1 and the second point on the first thread-like member L1 farther than the first point from the needle 30 in the direction from the first point toward the second point. The first operating shaft 20 of the embodiment is operated in this manner.

The suturing device 10 according to the present embodiment described above includes: a needle 30; and a shuttle 26. The needle 30 has an elongated shape extending in a predetermined direction and is configured to hold a first thread-like member L1. The needle is reciprocally movable forward and backward in the predetermined direction and is rotatable about an axis extending in the predetermined direction. Rotation of the needle 30 about the axis permitting the first thread-like member L1 to cross the needle 30 to form a loop LP in the first thread-like member L1. The shuttle 26 includes a holding part 62. The holding part 62 is configured to hold a second thread-like member L2. The shuttle is configured to permit the holding part 62 to pass through the loop LP. Thus, when the shuttle 26 passes the holding part 62 relative to the loop LP formed to intersect the needle 30, the second thread-like member L2 held in the holding part 62 and the loop LP cross each other, thereby easily and reliably forming a knot through mechanical operations based on simple manipulations.

The suturing device 10 in the present embodiment further includes a hollow cylindrical member 12. The cylindrical member 12 has an elongated shape extending in the predetermined direction. The cylindrical member 12 has a cylindrical tubes 12a and 12b. A direction from the cylindrical tube 12b to the cylindrical tube 12a is the predetermined direction. The cylindrical tube 12a is positioned forward than the cylindrical tube 12b in the predetermined direction. The needle 30 has a distal end and is configured to permit the first thread-like member L1 extending from the distal end to be shaped into the loop LP when the needle 30 moves backward in the longitudinal direction. Since the loop LP is formed by the first thread-like member L1 extending out from the distal end of the needle 30 when the reciprocated needle 30 moves backward, i.e., is retracted, the loop LP can be more easily formed than when using a transfer mechanism for the needle 30.

In the suturing device 10 according to the present embodiment, the cylindrical member 12 has a needle guide groove 40. The needle guide groove 40 is configured to guide the needle 30 in the predetermined direction. Through this construction, the needle 30 configured of a thin hollow tube can be stabilized by the needle guide groove 40 at any position along the path K of the distal end of the needle 30, thereby enhancing the precision of the stitches N.

The suturing device 10 according to the present embodiment further includes a friction member 42. The friction member 42 is disposed in the needle guide groove 40 and contactable with the needle 30. Through contact with the friction member 42, the first thread-like member L1 led out from the distal end of the needle 30 forms a loop LP on the distal end of the needle 30 when the needle 30 is retracted.

The suturing device 10 according to the present embodiment further includes: a depression 34; and a suturing target clamping mechanism 78. The depression 34 is provided at the cylindrical member 12 and is configured to receive a biological tissue T as a suturing target. The suturing target clamping mechanism 78 is provided in the cylindrical member 12 and is configured to place the biological tissue T in contact with the depression 34 and to immobilize the biological tissue T relative to the cylindrical member 12. Using the suturing target clamping mechanism 78 to immobilize the biological tissue T in contact with the depression 34 in this way reduces any shifting of the biological tissue T during suturing, thereby improving the quality of the sutures formed in the biological tissue T. Further, since the suturing target clamping mechanism 78 is configured of a balloon (expanding bag) 78a provided on the rear surface of the cylindrical member 12 at a position corresponding to the region in which the depression 34 is formed, the biological tissue T can be fixed in the depression 34 through a simple construction.

The suturing device 10 according to the present embodiment further includes a hook member 28. The hook member 28 is positioned in the cylindrical member 12 and is movable in the predetermined direction. Both of the first thread-like member L1 and the second thread-like member L2 are parts of a single thread-like member L. The hook member 28 is configured to hook a first portion L1 of the single thread-like member L positioned between the needle 30 and the shuttle 26. Therefore, the formation of a plurality of stitches N is completed by forming a knot M after the last stitch N, without requiring formation of a knot M prior to the initial stitch N. Further, by retracting the hook member 28 while the hook member 28 is hooked around a second portion L2 of the thread-like member L between the needle 30 and the shuttle 26, the shuttle 26 can be passed through the loop LP without interference from the thread-like member L.

The suturing device 10 according to the present embodiment further includes: a second operating shaft 22; and a third operating shaft 24. The second operating shaft 22 is connected to the needle 30. The second operating shaft is configured to reciprocally move the needle 30 in the predetermined direction and to rotate the needle 30 about an axis of the needle 30. The third operating shaft 24 is connected to the hook member 28. The third operating shaft 24 is configured to reciprocally move the hook member 28 in the predetermined direction and to rotate the hook member 28 about an axis of the hook member 28. Therefore, the needle 30 can be reciprocated along the path K by operating the second operating shaft 22 so that the second operating shaft 22 is reciprocated along the longitudinal direction of the cylindrical member 12. Further, the first thread-like member L1 can be wrapped around the needle 30 by operating the second operating shaft 22 so that the second operating shaft 22 rotates the needle 30 about its axis. A loop LP is formed on the needle 30 by operating the second operating shaft 22 so that the needle 30 around which the first thread-like member L1 is wound moves toward the retracted side. Further, by rotating the third operating shaft 24 in order to rotate the hook member 28, the hook member 28 can be detached from the second thread-like member L2 held in the holding part 62 of the shuttle 26, and by operating the third operating shaft 24 in the longitudinal direction of the cylindrical member 12 so as to move the hook member 28 in the retracting direction, slack can be formed in the second thread-like member L2 held in the holding part 62 of the shuttle 26. These operations can prevent the second thread-like member L2 from becoming entangled when the shuttle 26 is threaded through the loop LP. Further, the hook member 28 can be rotated and detached from the second thread-like member L2 when the shuttle 26 is moved in the retracting direction by the first operating shaft 20. Further, slack can once again be formed in the second thread-like member L2 by first moving the shuttle 26 in the advancing direction through the first operating shaft 20 and subsequently rotating the hook member 28 to hook the second thread-like member L2 that has been passed through the loop LP.

In the suturing device 10 according to the present embodiment, the shuttle 26 has one end portion provided with a first hook-shaped end 64. The first hook-shaped end 64 is configured to acquire the loop LP. The first hook-shaped end 64 is configured to permit the second thread-like member L2 to pass through the loop LP. In this way, the shuttle 26 having the holding part 62 that holds the second thread-like member L2 can be easily passed through the loop LP formed at the distal end portion of the needle 30.

According to the suturing device 10 of the present embodiment, the shuttle 26 has another end portion provided with a second hook-shaped end 66. The second hook-shaped end 66 is configured to acquire the loop LP. The second hook-shaped end 66 is configured to permit the second thread-like member L2 to pass through the loop LP. The first hook-shaped end 64 and the second hook-shaped end 66 are positioned opposite to each other with respect to the holding part 62. In this way, the shuttle 26 can easily pass through the loop LP formed on the needle 30 in both right-hand and left-hand rotating directions.

In the suturing device 10 according to the present embodiment, the first hook-shaped end 64 has a first end with an acutely angled tip. The first hook-shaped end 64 tapers away from the holding part 62 toward the first end. The second hook-shaped end 66 has a second end with an acutely angled tip. The second hook-shaped end 66 tapers away from the holding part 62 toward the second end. This shape allows the shuttle 26 to easily acquire the loop LP formed on the distal end portion of the needle 30, even when the shape of the loop LP varies.

The suturing device 10 according to the present embodiment further includes: a shuttle guide member 36; and a first operating shaft 20. The shuttle guide member 36 has a cylindrical shape extending in the predetermined direction and provides a center axis C1 extending in the predetermined direction. The first operating shaft 20 is rotatable about the center axis C1 to operate the shuttle 26. Rotation of the first operating shaft 20 in a right-hand (first) rotating direction about the center axis C1 permits the shuttle 26 to pass through the loop LP such that the first hook-shaped end 64 is a leading end in the movement of the shuttle 26. Rotation of the first operating shaft 20 in a left-hand (second) rotating direction opposite to the first rotating direction about the center axis C1 permits the shuttle 26 to pass through the loop LP such that the second hook-shaped end 66 is a leading end in the movement of the shuttle 26. Since the shuttle 26 can be passed through the loop LP formed at the distal end portion of the needle 30 each time the shuttle 26 is reciprocated in a circumferential direction about the center axis C1 of the shuttle guide member 36 in this way, the shuttle 26 need not be reciprocated after forming each stitch N, thereby simplifying suturing operations.

The suturing device 10 according to the present embodiment further includes a first operating shaft 20. The first operating shaft 20 is configured to move the shuttle 26. The first thread-like member L1 has a first intersecting point P1 and a second intersecting point P2. The second intersecting point P2 is positioned farther from the needle 30 than the first intersecting point P1 and is overlapped with the first intersecting point P1 to form the loop LP between the first intersecting point P1 and the second intersecting point P2.

The first operating shaft 20 is configured to move the shuttle 26 so that the holding part 62 passes through the loop LP in a direction from the first intersecting point P1 to the second intersecting point P2. By operating the first operating shaft 20 in this way so that the holding part 62 of the shuttle 26 holding the second thread-like member L2 is passed through the loop LP, which is formed by the first intersecting point A of the first thread-like member L1 nearer the biological tissue T intersecting the second intersecting point B of the first thread-like member L1 farther from the biological tissue T, in a direction from the side of the second intersecting point B to the side of the first intersecting point A, the second thread-like member L2 can be passed through the loop LP formed by the first thread-like member L1, thereby easily forming a single stitch N or knot M.

The suturing device 10 according to the present embodiment further includes: a shuttle guide member 36; and a pusher 58. The shuttle guide member 36 has a cylindrical shape extending in the predetermined direction and providing a circumferential direction and a center axis C1 extending in the predetermined direction. The shuttle guide member 36 is configured to guide the shuttle 26 in the circumferential direction. The pusher 58 is configured to move the shuttle 26 about the center axis C1. With this configuration, the shuttle 26 can be passed through a loop LP formed at the distal end portion of the needle 30 by rotating the first operating shaft 20 about the center axis C1.

In the suturing device 10 according to the embodiment, the shuttle guide member 36 includes a shuttle guide groove 56. The shuttle guide groove 56 is formed into an annular shape and is configured to guide the shuttle 26 in the circumferential direction. With this configuration, the shuttle 26 can be passed through the loop LP formed on the needle 30 while being guided in the circumferential direction by the shuttle guide groove 56.

In the suturing device 10 of the present embodiment, the pusher 58 is spaced away in the circumferential direction from the shuttle 26 guided by the shuttle guide groove 56 in the circumferential direction. This configuration can absorb any variation in the amount that the first operating shaft 20 is operated when the first operating shaft 20 is operated in the right-hand (first) rotating direction to move the shuttle 26.

In the suturing device 10 according to the present embodiment, the shuttle has an arcuate shape with a circumferential length corresponding to an angle less than 180 degrees whose vertex is the center axis C1. In this way, the shuttle 26 can be passed through the loop LP formed at the distal end portion of the needle 30 each time the shuttle 26 is reciprocated in the circumferential direction about the center axis C1 of the shuttle guide member 36.

In the suturing device 10 according to the present embodiment, the needle 30 has a distal end. The distal end of the needle 30 reciprocally moves along a path K extending in the predetermined direction in the reciprocal movement of the needle 30 in the predetermined direction. The shuttle guide member 36 has a loop support space. The loop space is in communication with the shuttle guide groove 56 and is configured to accommodate therein the first thread-like member L1 positioned on the path K. With this configuration, the first thread-like member L1 positioned on the path K can be prevented from interfering with other members, and the loop LP in the first thread-like member L1 formed on the needle 30 can be positioned inside the shuttle guide groove 56.

The suturing device 10 according to the present embodiment further includes: a hollow cylindrical member 12; and a first operating shaft 20. The cylindrical member 12 has an elongated shape extending in the predetermined direction. The first operating shaft 20 has an end portion positioned frontward in the predetermined direction. The first operating shaft 20 is configured to move the shuttle 26. The shuttle guide member 36 includes: a shuttle guide main body 52; and a shuttle guide pressing member 54. The shuttle guide main body 52 is reciprocally movable along the center axis C1 relative to the cylindrical member 12. The end portion of the first operating shaft 20 penetrates through the shuttle guide main body 52. The shuttle guide main body 52 is formed with the slit 76 providing a loop support space. The loop support space is positioned inward of the path K and is configured to accommodate therein the loop LP. The shuttle guide pressing member 54 is fixed to the shuttle guide main body 52 and forms the shuttle guide groove 56 in cooperation with the shuttle guide main body 52 to guide the shuttle 26 in the circumferential direction. This configuration can maintain the shape of the loop LP formed on the needle 30 so that the loop LP is not interfered with by other members and does not get in the way of other members.

The suturing device 10 according to the present embodiment further includes: a hollow cylindrical member 12; a shuttle guide member 36; a pusher 58; and a first operating shaft 20. The cylindrical member 12 has an elongated shape extending in the predetermined direction. The cylindrical member 12 provides a circumferential direction and a center axis C1 extending in the predetermined direction. The shuttle guide member 36 is fitted within the cylindrical member 12 and has a cylindrical shape extending in the predetermined direction. The shuttle guide member 36 is movable relative to the cylindrical member 12 along the center axis C1 and is non-rotatable relative to the cylindrical member about the center axis C1. The shuttle guide member 36 includes a shuttle guide groove 56. The shuttle guide groove 56 is formed into an annular shape. The shuttle guide groove 56 is configured to guide the shuttle 26 in the circumferential direction. The pusher 58 is configured to move the shuttle 26 about the center axis C1. The first operating shaft 20 has an end portion connected to the shuttle guide member 36 such that the end portion is immovable relative to the shuttle guide member 36 along the center axis C1 and is rotatable relative to the shuttle guide member 36 about the center axis C1. The pusher is fixed to the end portion of the first operating shaft 20. The first thread-like member L1 has a first intersecting point P1 and a second intersecting point P2. The second intersecting point P2 is positioned farther from the needle 30 than the first intersecting point P1 is from the needle 30 and is overlapped with the first intersecting point P1 to form the loop LP between the first intersecting point P1 and the second intersecting point P2. The first operating shaft 20 is configured to move the shuttle 26 so that the holding part 62 of the shuttle 26 passes through the loop LP in a direction from the first intersecting point P1 to the second intersecting point P2. With this configuration, the first operating shaft 20 can be rotated about the center axis C1 in order to move the shuttle 26 in a circumferential direction so as to be threaded through the loop LP. Further, by operating the first operating shaft 20 in a direction along the center axis C1, the shuttle 26 can be moved toward the proximal side of the cylindrical member 12 to tighten the second thread-like member L2 held in the holding part 62 of the shuttle 26.

In the suturing device 10 according to the present embodiment, the pusher 58 has an arcuate shape with a circumferential length corresponding to an angle less than 180 degrees whose vertex is the center axis C1. Hence, by using the pusher 58 to move in a circumferential direction the shuttle 26 having an arcuate shape with a circumferential length that corresponds to an angle less than 180 degrees whose vertex is the center axis C1, the shuttle 26 can be passed through the loop LP formed at the distal end portion of the needle 30 each time the shuttle 26 is reciprocated in a circumferential direction about the center axis C1 of the shuttle guide member 36.

In the suturing device 10 of the present embodiment, the needle 30 is constituted by a tubule. The tubule has an opening 68 positioned at the distal end portion of the tubule. The first thread-like member passes through the tubule and is exposed to an outside of the needle 30 through the opening 68. Accordingly, by passing the first thread-like member L1 through both the needle 30 and the biological tissue T, the first thread-like member L1 is exposed outside the biological tissue T at a position on the advanced side of the path K for the needle 30.

In the suturing device 10 of the present embodiment, the needle is constituted by a tubule, such as a needle 130 or needle 230. The needle 130/230 has an opening 70/72 positioned at a peripheral wall of the needle 130, 230. The first thread-like member L1 passing through the needle 130, 230 and is exposed to an outside of the needle 130, 230 through the opening 70, 72. Accordingly, by passing the first thread-like member L1 through both the needle 130/230 and the biological tissue T, the first thread-like member L1 is exposed outside the biological tissue T at a position on the advanced side of the path K for the needle 130/230.

While the description has been made in detail with reference to specific embodiments thereof, it would be apparent to those skilled in the art that many modifications and variations may be made thereto.

For example, the first thread-like member L1 and second thread-like member L2 in the embodiment described above may be any of various suture materials that can be tied, and preferably natural sutures formed by braiding natural plant-based or animal-based fibers, polymer sutures formed of monofilament or braided strands of synthetic fibers, metallic sutures formed of monofilament or braided metallic strands, or composite sutures formed of natural and synthetic fibers.

While the needle 30 is rotated only one time in the first stage for forming the knots M1 and M2 in the present embodiment described above in order to wrap the first thread-like member L1 around the needle 30, the needle 30 may instead by rotated two or more times. This action can achieve a more secure knot.

Similarly, while the shuttle 26 is passed only one time through the loop LP formed on the needle 30 with the first thread-like member L1 when forming the knots M1 and M2 in the present embodiment described above, the shuttle 26 instead may be passed two or more times through the loop LP. This method can form an even more secure knot.

In the embodiment described above, the cylindrical member 12 is used as the casing having an elongated shape, but the member used as the casing may be another type of cylindrical member, such as a square cylinder member having a polygonal shaped cross section or an elliptic cylinder member having an elliptical cross section.

In the embodiment described above, the first operating handle 21, second operating handle 23, and third operating handle 25 are provided for performing manual operations to advance, retract, or rotate the first operating shaft 20, second operating shaft 22, and third operating shaft 24. However, in order to perform these operations automatically, electric motors, hydraulic cylinders, and other actuators may be provided for the first operating shaft 20, second operating shaft 22, and third operating shaft 24. The drive of the actuators may be controlled according to pre-stored programs to achieve the operations described in FIGS. 34, 47, and 48, for example.

When forming a stitch N in the embodiment described above, the needle 30 is advanced without rotating and retracted to form the loop LP through which the shuttle 26 is passed, but the shuttle 26 may be passed through the loop LP formed by retracting the needle 30 after the needle 30 has been advanced with rotation. In this case, the first thread-like member L1 (bobbin thread (lower thread)) in FIG. 52 is crossed inside the biological tissue T. This is advantageous in that each stitch N forms a knot.

The depression 34 in the embodiment described above is formed in the circumferential wall 32 of the cylindrical member 12 functioning as the casing and is provided with an opening 34d that is open in the outer wall surface of the circumferential wall 32 of the cylindrical member 12. However, the casing may include a base part, a support column erected from the base part, and an arm part supported on the support column so as to be parallel to the base part, for example. When the needle is reciprocated along a path between the base part and the arm part, the base part and the space surrounded by the base part, support column, and arm part function as the depression. This type of depression is not provided with what was termed an opening in the embodiment.

In the embodiment described above, the shuttle 26 integrally configured of the holding part 62 holding the second thread-like member L2 and the first and second hook-shaped ends 64 and 66 is threaded through the loop LP, but the shuttle 26 need not pass through the loop LP. For example, the first and second hook-shaped ends 64 and 66 may be configured separately from the holding part 62, and the holding part 62 alone may be passed through the loop LP.

In the embodiment described above, the shuttle guide groove 56 having a concave cross section is provided in the shuttle guide member 36 for guiding the shuttle 26 in the longitudinal direction of the shuttle 26, i.e., in a circumferential direction around the center axis C1. However, the shuttle guide groove 56 need not have a concave cross section, but may have another shape capable of guiding the shuttle 26 along its longitudinal direction. For example, the shuttle guide groove 56 may be configured of a convex guide rail, peripheral walls, or the like, as long as the guide portion can guide the shuttle 26 along its longitudinal direction.

Although other examples of the description will not be illustrated herein, the description can be implemented in variously modified or refined forms based on the knowledge of those skilled in the art.

What is claimed is:

1. A suturing device comprising:
   a needle having an elongated shape extending in a predetermined direction and configured to hold a first thread-like member, the needle being reciprocally movable forward and backward in the predetermined direction and rotatable about an axis extending in the predetermined direction, rotation of the needle about the axis permitting the first thread-like member to cross the needle to form a loop in the first thread-like member;
   a shuttle including a holding portion configured to hold a second thread-like member, the shuttle being configured to permit the holding portion to pass through the loop;
   a shuttle guide member having a cylindrical shape extending in the predetermined direction and providing a circumferential direction and a center axis extending in the predetermined direction, the shuttle guide member being configured to guide the shuttle in the circumferential direction;
a pusher configured to move the shuttle about the center axis;
a hollow cylindrical member having an elongated shape extending in the predetermined direction; and
a shuttle operating shaft having an end portion positioned frontward in the predetermined direction, the shuttle operating shaft being configured to move the shuttle,
wherein the shuttle guide member comprises
a main body reciprocally movable along the center axis relative to the hollow cylindrical member, the end portion of the shuttle operating shaft penetrating through the main body, the main body being formed with the space positioned inward of the path and configured to accommodate therein the loop, and
a head fixed to the main body and forming the guide portion in cooperation with the main body to guide the shuttle in the circumferential direction,
wherein the needle has a tip end reciprocally moving along a path extending in the predetermined direction in the reciprocal movement of the needle in the predetermined direction,
wherein the shuttle guide member has a space in communication with the guide portion and configured to accommodate therein the first thread-like member positioned on the path, and
wherein the shuttle guide member includes a guide portion formed into an annular shape and configured to guide the shuttle in the circumferential direction.

2. The suturing device according to claim 1, wherein the hollow cylindrical member has a proximal end portion and a distal end portion, a direction from the proximal end portion to the distal end portion being the predetermined direction, the distal end portion being positioned forward than the proximal end portion in the predetermined direction, and
wherein the needle is configured to permit the first thread-like member extending from the tip end to be shaped into the loop when the needle moves backward in the longitudinal direction.

3. The suturing device according to claim 2, wherein the hollow cylindrical member has a guide groove configured to guide the needle in the predetermined direction.

4. The suturing device according to claim 3, further comprising a friction member disposed in the guide groove and contactable with the needle.

5. The suturing device according to claim 2, further comprising:
a depression provided at the hollow cylindrical member and configured to receive a suturing target; and
a clamping mechanism provided in the hollow cylindrical member and configured to place the suturing target in contact with the depression and to immobilize the suturing target relative to the hollow cylindrical member.

6. The suturing device according to claim 2, further comprising a hook member positioned in the hollow cylindrical member and movable in the predetermined direction,
wherein both of the first thread-like member and the second thread-like member are parts of a single thread-like member, the hook member being configured to hook a part of the single thread-like member positioned between the needle and the shuttle.

7. The suturing device according to claim 6, further comprising:
a needle operating shaft connected to the needle, the needle operating shaft being configured to reciprocally move the needle in the predetermined direction and to rotate the needle about an axis of the needle; and
a hook operating shaft connected to the hook member, the hook operating shaft being configured to reciprocally move the hook member in the predetermined direction.

8. The suturing device according to claim 1, wherein the shuttle has one end portion provided with a first hook-shaped portion configured to acquire the loop, the first hook-shaped portion being configured to permit the second thread-like member to pass through the loop.

9. The suturing device according to claim 8, wherein the shuttle has another end portion provided with a second hook-shaped portion configured to acquire the loop, the second hook-shaped portion being configured to permit the second thread-like member to pass through the loop, the first hook-shaped portion and the second hook-shaped portion being positioned opposite to each other with respect to the holding portion.

10. The suturing device according to claim 9, wherein the first hook-shaped portion has a first end with an acutely angled tip, the first hook-shaped portion tapering away from the holding portion toward the first end, and
wherein the second hook-shaped portion has a second end with an acutely angled tip, the second hook-shaped portion tapering away from the holding portion toward the second end.

11. The suturing device according to claim 9, wherein the shuttle operating shaft is rotatable about the center axis to operate the shuttle, rotation of the shuttle operating shaft in a first rotating direction about the center axis permitting the shuttle to pass through the loop such that the first hook-shaped portion is a leading end in the movement of the shuttle, rotation of the shuttle operating shaft in a second rotating direction opposite to the first rotating direction about the center axis permitting the shuttle to pass through the loop such that the second hook-shaped portion is a leading end in the movement of the shuttle.

12. The suturing device according to claim 1, wherein the first thread-like member has a first point and a second point positioned farther from the needle than the first point is from the needle and overlapped with the first point to form the loop between the first point and the second point, the shuttle operating shaft being configured to move the shuttle so that the holding portion passes through the loop in a direction from the first point to the second point.

13. The suturing device according to claim 1, wherein the pusher has an arcuate shape with a circumferential length corresponding to an angle less than 180 degrees whose vertex is the center axis.

14. The suturing device according to claim 1, wherein the pusher is spaced away in the circumferential direction from the shuttle guided by the guide portion in the circumferential direction.

15. The suturing device according to claim 1, wherein the shuttle has an arcuate shape with a circumferential length corresponding to an angle less than 180 degrees whose vertex is the center axis.

16. The suturing device according to claim 1, wherein the needle is constituted by a tubule having an opening positioned at a tip end portion of the tubule, the first thread-like member passing through the tubule and being exposed to an outside of the needle through the opening.

17. The suturing device according to claim 1, wherein the needle is constituted by a tubule having an opening positioned at a peripheral wall of the tubule, the first thread-like member passing through the tubule and being exposed to an outside of the needle through the opening.

18. A suturing device comprising:
- a needle having an elongated shape extending in a predetermined direction and configured to hold a first thread-like member, the needle being reciprocally movable forward and backward in the predetermined direction and rotatable about an axis extending in the predetermined direction, rotation of the needle about the axis permitting the first thread-like member to cross the needle to form a loop in the first thread-like member;
- a shuttle including a holding portion configured to hold a second thread-like member, the shuttle being configured to permit the holding portion to pass through the loop;
- a hollow cylindrical member having an elongated shape extending in the predetermined direction, the hollow cylindrical member providing a circumferential direction and a center axis extending in the predetermined direction;
- a shuttle guide member fitted within the hollow cylindrical member and having a cylindrical shape extending in the predetermined direction, the shuttle guide member being movable relative to the hollow cylindrical member along the center axis and non-rotatable relative to the hollow cylindrical member about the center axis, the shuttle guide member including a guide portion formed into an annular shape, the guide portion being configured to guide the shuttle in the circumferential direction;
- a pusher configured to move the shuttle about the center axis; and
- a shuttle operating shaft having an end portion connected to the shuttle guide member such that the end portion is immovable relative to the shuttle guide member along the center axis and rotatable relative to the shuttle guide member about the center axis, the pusher being fixed to the end portion,
- wherein the first thread-like member has a first point and a second point positioned farther from the needle than the first point is from the needle and overlapped with the first point to form the loop between the first point and the second point, the shuttle operating shaft being configured to move the shuttle so that the holding portion passes through the loop in a direction from the first point to the second point.

* * * * *

UNITED STATES PATENT AND TRADEMARK OFFICE
CERTIFICATE OF CORRECTION

| | |
|---|---|
| PATENT NO. | : 11,261,551 B2 |
| APPLICATION NO. | : 16/280344 |
| DATED | : March 1, 2022 |
| INVENTOR(S) | : Yuji Sakano et al. |

It is certified that error appears in the above-identified patent and that said Letters Patent is hereby corrected as shown below:

In the Claims

Claim 1, Column 29, Line 17:
Please change: "with the space positioned inward of the path and" to -- with a space positioned inward of a path and --

Claim 1, Column 29, Line 19:
Please change: "a head fixed to the main body and forming the guide" to -- a head fixed to the main body and forming a guide --

Claim 1, Column 29, Line 23:
Please change: "along a path extending in the predetermined direction" to -- along the path extending in the predetermined direction --

Claim 1, Column 29, Lines 26-27:
Please change: "wherein the shuttle guide member has a space in communication with the guide portion and configured to" to -- wherein the shuttle guide member has the space in communication with the guide portion and configured to --

Claim 1, Column 29, Lines 30-31:
Please change: "wherein the shuttle guide member includes a guide portion formed into an annular shape and configured to" to -- wherein the shuttle guide member includes the guide portion formed into an annular shape and configured to --

Signed and Sealed this
Sixth Day of December, 2022

Katherine Kelly Vidal
*Director of the United States Patent and Trademark Office*